(12) United States Patent
Ntambi et al.

(10) Patent No.: US 7,285,395 B2
(45) Date of Patent: Oct. 23, 2007

(54) STEAROYL-COA DESATURASE 4 GENE

(75) Inventors: James M. Ntambi, Madison, WI (US); Makoto Miyazaki, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/147,606

(22) Filed: Jun. 8, 2005

(65) Prior Publication Data

US 2005/0278795 A1 Dec. 15, 2005

Related U.S. Application Data

(60) Provisional application No. 60/578,234, filed on Jun. 9, 2004.

(51) Int. Cl.
*C12Q 1/26* (2006.01)
*C12N 9/04* (2006.01)
*C12N 15/09* (2006.01)
*C07H 21/04* (2006.01)

(52) U.S. Cl. .................. 435/25; 435/69.1; 435/325; 435/320.1; 435/190; 536/23.2

(58) Field of Classification Search ............ 435/69.1, 435/189
See application file for complete search history.

(56) References Cited

U.S. PATENT DOCUMENTS

| 2003/0064950 A1 | 4/2003 | Ntambi et al. |
| 2003/0157552 A1 | 8/2003 | Hayden et al. |
| 2004/0072877 A1 | 4/2004 | Ntambi et al. |

OTHER PUBLICATIONS

Miyazaki et al. (JBC Jun. 2003, pp. 33904-33911).*
Targeted Disruption of Stearoyl-CoA Desaturase 1 Gene in Mice . . . ; Miyazaki, M. et al. (2001) J. Nutr. 131, 2260-2268.
Oleoyl-CoA is the Major de Novo Product of Stearoyl-CoA Desaturase 1 Gene Isoform . . . ; Miyazaki, M. et al. (2001) J. Biol. Chem. 276, 39455-39461.
Human Stearoyl-CoA Desaturase: Alternative Transcripts Generated from a Single Gene . . . ; Zhang, L. et al. (1999) Biochem. J. 340, 255-264.
Differentiation-induced Gene Expression in 3T3-L1 Preadipocytes; Ntambi, J. M. et al. (1988) J. Biol. Chem. 263, 17291-17300.
Scd3—A Novel Gene of the Stearoyl-CoA Desaturase Family with Restricted Expression in Skin; Zheng, Y. et al. (2001) Genomics 71, 182-191.
Identification and Characterization of a Novel Gene Disrupted by a Pericentric Inversion . . . ; Beiraghi, S. et al. (2003) Gene 309, 11-21.
Identification and Characterization of Murine SCD4 . . . ; Miyazaki, M. et al. (2003) J. Biol. Chem. 278, 33904-33911.
Differentiation-induced Gene Expression in 3T3-L1 Preadipocytes; Kaestner, K. H. et al. (1989) J. Biol. Chem. 264, 14755-14761.
*Mus musculus* Stearoyl-CoA Desaturase 4; GenBank Accession No. NM_183216, Apr. 2, 2004.
*Homo sapiens* Stearoyl-CoA Desaturase 4; GenBank Accession No. NM_024906, Jan. 1, 2004.

* cited by examiner

*Primary Examiner*—Rebecca E. Prouty
*Assistant Examiner*—Md. Y. Meah
(74) *Attorney, Agent, or Firm*—Quarles & Brady LLP

(57) ABSTRACT

The cloning of a fourth mouse SCD gene, mSCD4, as well as its corresponding cDNA and amino acid sequences are disclosed. Mouse SCD4 is expressed mainly in the heart tissue and synthesizes the bulk of monounsaturated fatty acids in the heart. The disclosure here enables new tools (e.g., nucleic acids, polypeptides, antibodies, vectors, recombinant cells, and transgenic and knock-out animals) for studying the function of various SCD isoforms and their connection to various disease conditions. New tools for converting saturated fatty acyl-CoA to monounsaturated acyl-CoA and for identifying SCD modulators including isoform-specific modulators are also enabled. In addition, given that accumulation of lipid in the heart (fatty heart) can have deleterious consequences, the present invention also provides a new prevention and treatment target for fatty heart as well as methods for screening candidate drugs.

4 Claims, 7 Drawing Sheets

Figure 2
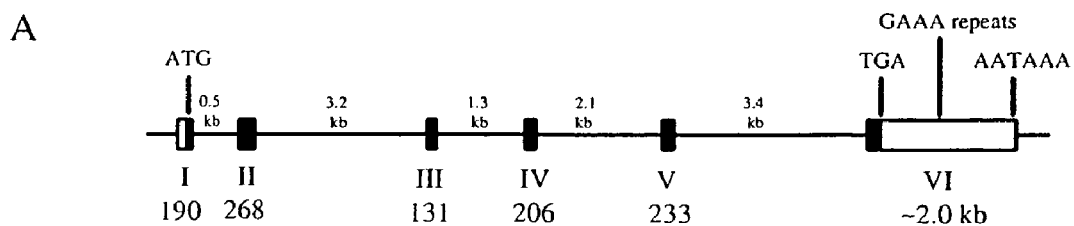
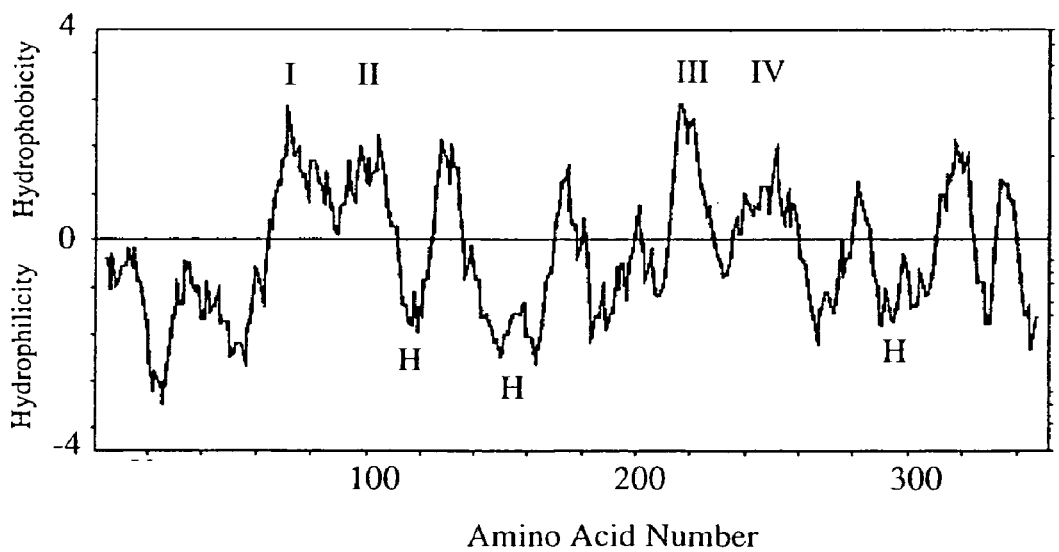

STEAROYL-CoA DESATURASE 4 GENE

CROSS-REFERENCE TO RELATED APPLICATIONS

This application claims the benefit of U.S. provisional application 60/578,234, filed on Jun. 9, 2004, which is incorporated by reference in its entirety.

STATEMENT REGARDING FEDERALLY SPONSORED RESEARCH OR DEVELOPMENT

This invention was made with United States government support awarded by the following agency: NIH DK062388. The United States has certain rights in this invention.

BACKGROUND OF THE INVENTION

Stearoyl-CoA desaturase (SCD) catalyzes the committed step in the biosynthesis of monounsaturated fatty acids from saturated fatty acids. This reaction involves the introduction of a cis-double bond in the Δ-9 position (between carbons 9 and 10) in a spectrum of methylene-interrupted fatty acyl-CoAs. The roles of monounsaturated fatty acids are diverse and crucial in living organisms. Palmitoleic and oleic acids are the major monounsaturated fatty acids in membrane phospholipids, triglycerides, and cholesterol esters (Miyazaki, M. et al. (2000) *J. Biol. Chem.* 275, 30132-30138). A proper ratio of saturated to monounsaturated fatty acids contributes to membrane fluidity, whereas changes in cholesterol esters and triglyceride levels affect lipoprotein and lipid metabolism (Miyazaki, M. et al. (2000) *J. Biol. Chem.* 275, 30132-30138; Feng, B. and Tabas, I. (2002) *J. Biol. Chem.* 277, 43271-43280; and Cohen, P. et al. (2002) *Science* 297, 240-243). Apart from being components of lipids, monounsaturated fatty acids have also been implicated as mediators in signal transduction and differentiation of neurons and other cells (Garbay, B. et al. (1998) *J. Neurochem.* 71, 1719-1726). Monounsaturated fatty acids have also been shown to regulate food intake in the brain (Obici, S. et al. (2002) *Diabetes* 51, 271-275). Given the multiple roles of monounsaturated fatty acids, alterations in SCD activity in mammals would be expected to have potent effects on lipid metabolism and to play a role in the propensity to develop obesity, atherosclerosis, and metabolic diseases (Miyazaki, M. and Ntambi, J. M. (2003) *Prostaglandins Leukotrienes Essent. Fatty Acids* 68, 113-121; and Ntambi, J. M. (1999) *J. Lipid Res.* 40, 1549-1558).

A number of mammalian SCD genes have been cloned and studied. Two SCD genes have been cloned in rats and three well characterized SCD genes (mSCD1, mSCD2, and mSCD3) have been cloned in mice (Ntambi, J. M. et al. (1988) *J. Biol. Chem.* 263, 17291-17300; Kaestner, K. H. et al. (1989) *J. Biol. Chem.* 264, 14755-14761; Zheng, Y. et al. (2001) *Genomics* 71, 182-191, all of which are herein incorporated by reference in their entirety). In addition, two human SCD genes, hSCD1 and hSCD5, have been cloned (Zhang, L. et al. (1999) *Biochem. J.* 340, 255-264; and Beiraghi, S. et al. (2003) *Gene* 309, 11-21). Human SCD1 is highly homologous to the mouse and rat SCDs.

It has been recently demonstrated that the regulation of SCD1 by leptin plays a crucial role in signaling the body to either store fat or burn it. Obese mice, which lack leptin, lost weight because of increased energy expenditure when genetically crossed with a strain of mice carrying a mutation in SCD1 (Cohen, P. et al. (2002) *Science* 297, 240-243). The missing SCD1 enzyme also corrected a major clinical problem called fatty liver, which is found in obese mice and humans. Leptin has also been found to reduce fat deposition in other tissues such as muscle and heart (Minokoshi, Y. et al. (2002) *Nature* 415, 339-343; Atkinson, L. L. et al. (2002) *J. Biol. Chem.* 277, 29424-29430; Zhou, Y. T. et al. (2000) *Proc. Natl. Acad. Sci. U.S.A.* 97, 1784-1789; and Unger, R. H. (2002) *Annu. Rev. Med* 53, 319-336).

The expression of different SCD isoforms varies among tissues. For example, mSCD1 is the main isoform expressed in the liver whereas mSCD2 is constitutively expressed in the brain (Ntambi, J. M. et al. (1988) *J. Biol. Chem.* 263, 17291-17300; and Kaestner, K. H. et al. (1989) *J. Biol. Chem.* 264, 14755-14761). In tissues such as the adipose and eyelids, both mSCD1 and mSCD2 are expressed. On the other hand, all three mouse isoforms are expressed in skin, Harderian, and preputial glands (Zheng, Y. et al. (2001) *Genomics* 71, 182-191; and Miyazaki, M. et al. (2001) *J. Biol. Chem.* 276, 39455-39461). The reason for having two or more SCD isoforms in the same tissue seems to be related to substrate specificity of the isomers and their regulation through tissue-specific transcription factors (Miyazaki, M. et al. (2001) *J. Nutr.* 131, 2260-2268).

It is of great interest in the art to identify other isoforms of SCD, if they exist, so that the expression pattern and regulation of all SCD isoforms can be studied and compared and their connection to various diseases and conditions be assessed. The identification of new SCD isoforms will further assist, among other things, the development of target-specific drugs, i.e., drugs that inhibit the activity of a disease-causing isoform but not other isoforms that perform important normal, physiological functions.

BRIEF SUMMARY OF THE INVENTION

The present invention is based on the cloning of a fourth mouse SCD gene, mSCD4, by the inventors. The mSCD4 cDNA and amino acid sequences are provided in SEQ ID NO:1 (nucleotides 167 to 1228) and SEQ ID NO:2, respectively. The mSCD4 gene encodes a 353-amino acid protein that shares 79% sequence identity with the mouse SCD1, SCD2, and SCD3 isoforms. Mouse SCD4 is expressed mainly in the heart tissue and it synthesizes the bulk of monounsaturated fatty acids in the heart. The disclosure here enables new tools (e.g., nucleic acids, polypeptides, antibodies, vectors, recombinant cells, and transgenic and knock-out animals) for studying the function of various SCD isoforms and their connection to various disease conditions. New tools for converting saturated fatty acyl-CoA to monounsaturated acyl-CoA and for identifying SCD modulators including isoform-specific modulators are also enabled. In addition, given that accumulation of lipid in the heart, i.e., fatty heart, can have deleterious consequences (Minokoshi, Y. et al. (2002) *Nature* 415, 339-343; Atkinson, L. L. et al. (2002) *J. Biol. Chem.* 277, 29424-29430; Zhou, Y. T. et al. (2000) *Proc. Natl. Acad. Sci. U.S.A.* 97, 1784-1789; and Unger, R. H. (2002) *Annu. Rev. Med* 53, 319-336, all of which are herein incorporated by reference in their entirety), the present invention also provides a prevention and treatment target for fatty heart and methods for screening candidate drugs.

BRIEF DESCRIPTION OF THE SEVERAL VIEWS OF THE DRAWINGS

FIG. 2 shows the structure of mSCD4. A, Gene structure of mSCD4. B, Amino acid sequence alignment of SCD4 and mouse SCD1, SCD2, and SCD3: The amino acid sequence of mSCD4 was deduced from cDNA sequence. The nonconserved amino acids are shaded in gray. The three HXXHH motifs that are 100% conserved are shaded in black. The transmembrane domain amino acids are underlined. C, Kyte and Doolittle hydropathy plot of mSCD4: The residue-specific hydropathy index was calculated over a window of 18 amino acids using DNA STAR software version 5.0. The four transmembrane domains are labeled I-IV, and the histidine motifs are denoted by H.

DETAILED DESCRIPTION OF THE INVENTION

Figure 1:
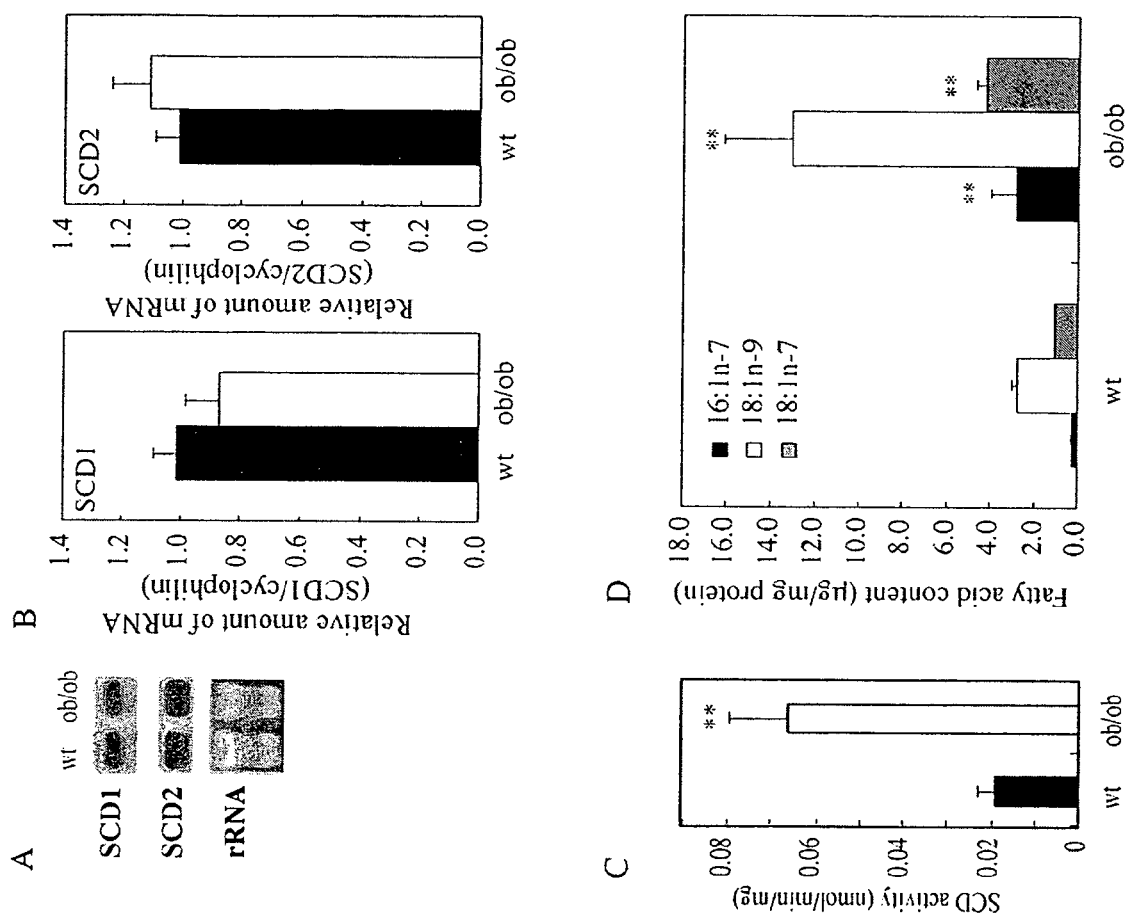
FIG. 1 shows the expression of SCD1 and SCD2 in the heart of ob/ob mice. A, Northern blot analysis of SCD1 and SCD2 gene isoforms: Total RNA prepared from hearts of wild type (wt) and ob/ob mice was used to measure the mRNA levels of SCD1 and SCD2 as described in the example below. B, quantitative RT-PCR analysis: The fold change relative to that of wild type was calculated after correction for the expression of cyclophilin used as a standard. C, SCD enzyme activity: Aliquots of microsome fractions (100 µg) from hearts of wild type and ob/ob mice were incubated with a reaction mixture containing [1-$^{14}$C] stearoyl-CoA for 5 min. The products were acidified, and the fatty acids were extracted and separated by TLC. Each value represents the mean±S.D. (n=5). D, levels of monounsaturated fatty acids: Total fatty acids were extracted from heart of wild type and ob/ob mice and quantitated by gas-liquid chromatography (GLC) as described in the example below. **, $p<0.001$ versus wild type (Student's t test).

I. Nucleic Acids, Vectors, Genetically Engineered Cells and Animals, Polypeptides, and Antibodies The term "isolated nucleic acid" or "isolated polypeptide" used in the specification and claims means a nucleic acid or polypeptide isolated from its natural environment or prepared using synthetic methods such as those known to one of ordinary skill in the art. Complete purification is not required in either case. Nucleotide or amino acid sequences that flank a nucleic acid or polypeptide in nature can but need not be absent from the isolated form. A nucleic acid and polypeptide of the invention can be isolated and purified from normally associated material in conventional ways such that in the purified preparation the nucleic acid or polypeptide is the predominant species in the preparation. At the very least, the degree of purification is such that the extraneous material in the preparation does not interfere with use of the nucleic acid or polypeptide of the invention in the manner disclosed herein. The nucleic acid or polypeptide is preferably at least about 85% pure, more preferably at least about 95% pure, and most preferably at least about 99% pure.

Further, an isolated nucleic acid has a structure that is not identical to that of any naturally occurring nucleic acid or to that of any fragment of a naturally occurring genomic nucleic acid spanning more than three separate genes. The term therefore covers, for example, (a) a DNA that has the sequence of part of a naturally occurring genomic DNA molecule but which is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a CDNA or genomic DNA library. An isolated nucleic acid molecule can be modified or unmodified DNA or RNA, whether fully or partially single-stranded or double-stranded or even triple-stranded. A modified nucleic acid molecule can be chemically or enzymatically induced and can include so-called non-standard bases such as inosine.

As used in this application, "percent identity" between amino acid or nucleotide sequences is synonymous with "percent homology," which can be determined using the algorithm of Karlin and Altschul (*Proc. Natl. Acad. Sci. USA* 87, 2264-2268, 1990), modified by Karlin and Altschul (*Proc. Natl. Acad. Sci. USA* 90, 5873-5877, 1993), or other methods, particularly those methods noted as appropriate throughout the application. The noted algorithm is incorporated into the NBLAST and XBLAST programs of Altschul et al. (*J. Mol. Biol.* 215, 403-410, 1990). BLAST nucleotide searches are performed with the NBLAST program, score=100, wordlength=12, to obtain nucleotide sequences homologous to a polynucleotide of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (*Nucleic Acids Res.* 25, 3389-3402, 1997). When utilizing BLAST and Gapped BLAST programs, the default parameters of the respective programs (e.g., XBLAST and NBLAST) are used.

In one aspect, the present invention relates to an isolated nucleic acid that contains an uninterrupted nucleotide coding sequence or its complement wherein the uninterrupted coding sequence encodes an amino acid sequence selected from SEQ ID NO:2, an amino acid sequence that is at least 90% identical to SEQ ID NO:2, or SEQ ID NO:2 with one or more conservative substitutions. It is well known in the art that the amino acids within the same conservative group can typically substitute for one another without substantially affecting the function of a protein. For the purpose of the present invention, such conservative groups are set forth in Table 1 based on shared properties.

TABLE 1

Conservative substitution.

| Original Residue | Conservative Substitution |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |

TABLE 1-continued

Conservative substitution.

| Original Residue | Conservative Substitution |
| --- | --- |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

In a preferred embodiment, the isolated nucleic acid contains an uninterrupted coding sequence or its complement wherein the coding sequence encodes an amino acid sequence that is at least 95%, at least 97%, at least 99%, or 100% identical to SEQ ID NO:2. In a more preferred embodiment, the coding sequence is nucleotides 167 to 1225 of SEQ ID NO:1.

An isolated nucleic acid containing a polynucleotide (or its complement) that is at least 90%, at least 95%, at least 97%, or at least 99% identical to any of the uninterrupted coding sequence described above is also within the scope of the present invention.

An isolated nucleic acid containing a polynucleotide (or its complement) that can hybridize to any of the uninterrupted coding sequence described above, under either stringent or moderately stringent hybridization conditions, is also within the scope of the present invention. Stringent hybridization conditions are defined as hybridizing at 68° C. in 5×SSC/5× Denhardt's solution/1.0% SDS, and washing in 0.2×SSC/0.1% SDS±100 µg/ml denatured salmon sperm DNA at room temperature, and moderately stringent hybridization conditions are defined as washing in the same buffer at 42° C. Additional guidance regarding such conditions is readily available in the art, for example, by Sambrook et al., 1989, *Molecular Cloning, A Laboratory Manual*, Cold Spring Harbor Press, N.Y.; and Ausubel et al. (eds.), 1995, *Current Protocols in Molecular Biology*, (John Wiley & Sons, N.Y.) at Unit 2.10.

In a related aspect, any nucleic acid of the present invention can be provided in a vector in a manner known to those skilled in the art. The vector can be a cloning vector or an expression vector. In an expression vector, the nucleotide coding sequence is under the transcriptional control of one or more non-native expression control sequences which can include a promoter not natively found adjacent to the coding sequence such that the encoded polypeptide can be produced when the vector is provided in a compatible host cell or in a cell-free transcription and translation system. Such cell-based and cell-free systems are well known to a skilled artisan. Cells, preferably heart cells (e.g., myocytes), comprising a vector containing a nucleic acid of the invention are themselves within the scope of the present invention. Also within the scope of the present invention is a host cell, preferably a heart cell (e.g., a myocyte), having the nucleic acid of the present invention integrated into its genome and the nucleic acid is operably linked to a non-native expression control sequence (e.g., a promoter).

In another related aspect, the present invention relates to a transgenic animal such as a transgenic mouse that comprises a nucleic acid of the present invention as described above operably linked to a non-native expression control sequence.

In another related aspect, the present invention relates to a genetically engineered mouse cell in which the mSCD4 nucleic acid sequence has been disrupted. For the purpose of the present invention, a disrupted SCD4 nucleic acid sequence means that it cannot produce a detectable level of functional SCD4 protein. In one embodiment, both chromosomal copies of the mSCD4 nucleic acid sequence have been disrupted in the cell.

In another related aspect, the present invention relates to a mouse heart cell (e.g., a myocyte) in which the SCD4 gene is inactivated by, for example, disrupting the SCD4 nucleic acid sequence. In another aspect, the present invention relates to a mouse that lacks expression of functional SCD4 protein by, for example, disrupting the SCD4 nucleic acid sequence.

The mouse SCD4 gene may be disrupted using a variety of technologies familiar to those skilled in the art. For example, a stop codon may be introduced into the gene by homologous recombination. Alternatively, a deletion may be introduced into the gene by homologous recombination. In some embodiments, stop codons may be introduced in all reading frames in the sequence downstream of the deletion to eliminate artifactual translation products. In further embodiments, the gene may be disrupted by inserting a gene encoding a marker protein, for example, therein via homologous recombination.

A skilled artisan is familiar with how a mouse or mouse cell with disrupted SCD4 gene, i.e., the knockout mouse or mouse cell, can be generated. For example, the generation of a knockout mouse can involve the production of a suitable gene-targeting vector, the isolation of correctly genetically modified embryonic stem cells, the provision of mouse blastocysts with these cells by way of injection, the establishment of chimeras and the pairing of these mice to generate mice having the desired genotype (A. L. Joyner: *Gene targeting: A practical approach*, Oxford University Press, Oxford, 1993, p. 1-234).

In addition to disrupting the SCD4 gene nucleic acid sequence as described above, the SCD4 gene can also be inactivated according to other methods known to a person skilled in the art. The use of the antisense technique or the injection of neutralizing antibodies are examples of such other methods.

In another aspect, the present invention relates to an isolated polypeptide that contains an amino acid sequence selected from SEQ ID NO:2, an amino acid sequence that is at least 90% identical to SEQ ID NO:2, or SEQ ID NO:2 with one or more conservative substitutions. Preferably, the isolated polypeptide contains an amino acid sequence that is at least 95%, at least 97%, at least 99%, or 100% identical to SEQ ID NO:2. In one embodiment, the isolated polypeptide of the present invention also contains a short peptide for purifying, detecting, or stabilizing the polypeptide.

In another aspect, the present invention relates to an antibody that is specific for a polypeptide that consists of an amino acid sequence selected from SEQ ID NO:2, an amino acid sequence that is at least 90% identical to SEQ ID NO:2, or SEQ ID NO:2 with one or more conservative substitutions. Preferably, the isolated polypeptide consists of an amino acid sequence that is at least 95%, at least 97%, at least 99%, or 100% identical to SEQ ID NO:2. By an antibody that is specific for the polypeptide described above, we mean that the antibody has a higher affinity (preferably at least one fold higher) for the polypeptide than for mSCD1, mSCD2, mSCD3, or a combination of any of the foregoing.

It is well within the ability of a skilled artisan to make such a monoclonal or polyclonal antibody and to assess the specificity of the antibody.

II. Methods for Converting Saturated Fatty Acyl-CoAs

In another aspect, the present invention relates to a method for converting a saturated fatty acyl-CoA to its corresponding monounsaturated fatty acyl-CoA by exposing the fatty acyl-CoA to mSCD4 under the conditions which allow the formation of the corresponding monounsaturated fatty acyl-CoA. Various such conditions are known in the art and other suitable conditions can be readily recognized or determined by a skilled artisan. Examples of suitable conditions can be found in Miyazaki, M. et al. (2001) *J. Biol. Chem.* 276, 39455-39461; and Miyazaki, M. et al. (2003) *J. Biol. Chem.* 278, 33904-33911, both of which are herein incorporated by reference in their entirety. Other examples of such conditions are described below. The formation of the above monounsaturated fatty acyl-CoAs can be observed by any known technique in the art. In one embodiment, myristoyl-CoA, pentadecanoyl-CoA, palmitoyl-CoA, margaroyl-CoA, stearoyl-CoA, nonadecanoyl-CoA, or a combination of any of the forgoing is converted to the corresponding monounsaturated fatty acyl-CoAs. In another embodiment, pentadecanoyl-CoA, palmitoyl-CoA, margaroyl-CoA, stearoyl-CoA, or a combination of any of the forgoing is converted to the corresponding monounsaturated fatty acyl-CoAs. In a preferred embodiment, palmitoyl-CoA, margaroyl-CoA, stearoyl-CoA, or a combination of any of the forgoing is converted to the corresponding monounsaturated fatty acyl-CoAs.

III. Preventing or Treating Fatty Heart

Based on the identification of the mouse SCD4 gene and its dominant expression in the heart tissue, it provides here that the fatty heart can be treated or prevented in a mouse by reducing the activity of SCD4 in the heart tissue as SCD4 is expected to play a major role in the production of monounsaturated fatty acids and triglycerides in the heart. It is expected that the method also applies to human beings. Although the human gene that corresponds to the mouse SCD4 gene has not been cloned, it is expected the corresponding human gene will be found highly homologous to the mouse SCD4 gene just as the human SCD1 gene was found highly homologous to the mouse SCD1 gene (87% identity at the amino acid level). Therefore, any mouse SCD4 inhibitor such as those identified by the screening method described below are considered candidate drugs for preventing and treating fatty heart in human beings. In addition, the various strategies described below for reducing mouse SCD4 activity also apply to reducing the activity of the corresponding human SCD protein. The term "prevent (preventing, prevented, and prevention)" is used broadly here to include delaying of the onset of a disease, reducing in the severity of a disease at the onset, or completely preventing the development of a disease.

Mouse SCD4 activity can be reduced through genetic manipulation or through the use of other inhibitors. Preferably, an inhibitor that does not significantly cross-inhibit other desaturases such as delta-5 and delta-6 desaturases, fatty acid synthetase, mSCD1, mSCD2, mSCD3, hSCD1, and hSCD5. An inhibitor can be administered orally, as a food supplement or adjuvant, or by any other effective means which has the effect of reducing SCD4 activity.

While it is envisaged that any suitable mechanism for reducing SCD4 activity can be used, three specific examples of reduction classes are envisioned. One class includes lowering SCD4 protein level. A second class includes the inhibition of SCD4 enzymatic activity. The third class includes interfering with the proteins essential to the desaturase system, such as cytochrome $b_5$, NADH (P)-cytochrome $b_5$ reductase, and terminal cyanide-sensitive desaturase.

Many strategies are available to lower SCD4 protein level. For example, one can increase the degradation rate of the enzyme or inhibit rate of synthesis of the enzyme. The synthesis of the enzyme can be inhibited at transcriptional level or translational level by known genetic techniques. For example, leptin can be used to inhibit SCD4 expression (example below).

One method to block SCD4 synthesis at the translational level is to use an antisense oligonucleotide (DNA or RNA) having a sequence complementary to at least part of a SCD4 mRNA sequence. One of ordinary skill in the art knows how to make and use an antisense oligonucleotide to block the synthesis of a protein (Agarwal, S. (1996) *Antisense Therapeutics*, Totowa, N.J., Humana Press, Inc.). An example of the antisense method for the present invention is to use 20-25 mer antisense oligonucleotides directed against 5' end of a SCD4 mRNA with phosphorothioate derivatives on the last three base pairs on the 3' end and the 5' end to enhance the half life and stability of the oligonucleotides. A useful strategy is to design several oligonucleotides with a sequence that extends 2-5 basepairs beyond the 5' start site of transcription.

An antisense oligonucleotide used for preventing or treating fatty heart can be administered intravenously into an animal. A carrier for an antisense oligonucleotide can be used. An example of a suitable carrier is cationic liposomes. For example, an oligonucleotide can be mixed with cationic liposomes prepared by mixing 1-alpha dioleylphatidylcelthan olamine with dimethldioctadecylammonium bromide in a ratio of 5:2 in 1 ml of chloroform. The solvent will be evaporated and the lipids resuspended by sonication in 10 ml of saline.

Another way to use an antisense oligonucleotide is to engineer it into a vector so that the vector can produce an antisense cRNA that blocks the translation of the mRNAs encoding for SCD4.

SCD4 monoclonal or polyclonal antibodies, or SCD4-binding fragments thereof, can be used as SCD4 inhibitors for the purpose of this invention. In one embodiment, the antibody is isolated, i.e., an antibody free of any other antibodies. Generally, it has been shown that an antibody can block the function of a target protein when administered into the body of an animal. Dahly, A.J. (2000) *FASEB J.* 14, A133; Dahly, A. J. (2000) *J. Am. Soc. Nephrology* 11, 332A. Thus, a SCD4 antibody can be used to treat or prevent fatty heart. For example, about 0.01 mg to about 100 mg, preferably about 0.1 mg to about 10 mg, and most preferably about 0.2 mg to about 1.0 mg of a humanized SCD4 antibody can be administered to a human being. The half life of these antibodies in a human being can be as long as 2-3 weeks.

An agent that interferes with a protein essential to the desaturase system can also be used to inhibit SCD4 activity. The desaturase system has three major proteins: cytochrome $b_5$, NADH (P)-cytochrome $b_5$ reductase, and terminal cyanide-sensitive desaturase. Terminal cyanide-sensitive desaturase is the product of the SCD gene. SCD activity depends upon the formation of a stable complex between the three aforementioned components. Thus, any agent that interferes with the formation of this complex or any agent that interferes with the proper function of any of the three components of the complex would effectively inhibit SCD4 activity.

IV. Screening Assays

A. Binding Assay

In another aspect, the present invention relates to a method for screening for agents that have the potential to modulate mSCD4 activity. The method involves providing a polypeptide of the present invention as described above (the preferred polypeptide is SEQ ID NO:2), exposing the polypeptide to a test agent, and determining whether the agent binds to the polypeptide. If an agent binds to the polypeptide, it is likely that the agent can modulate the activity of mSCD4. It is possible that not 100% of the positively identified agents from this screening assay will be able to modulate the activity of mSCD4. In this regard, a mSCD4 biological activity assay (described below) can be used to further determine whether the agent can modulate mSCD4 activity.

There are many systems in the art that a skilled artisan is familiar with for assaying the binding between a polypeptide and an agent. Any of these systems can be used in the method of the present invention. Detailed experimental conditions can be readily determined by a skilled artisan. For example, a polypeptide of the present invention can be provided on a suitable substrate and exposed to a test agent. The binding of the agent to the polypeptide can be detected either by the loss of ability of the polypeptide to bind to an antibody or by the labeling of the polypeptide if the agent is labeled with radioactivity, fluorescence or other features. In another example, a polypeptide of the present invention can be expressed in a host cell, e.g., a mouse cell, and the cell is then exposed to a test agent. Next, the polypeptide can be isolated, e.g., by immunoprecipitation or electrophoresis, and the binding between the polypeptide and the agent can be determined. As mentioned above, one way to determine the binding between the polypeptide and the agent is to label the agent with radioactivity or fluorescence so that the polypeptide that binds to the agent is radioactive or fluorescent. Detailed experimental conditions can be readily determined by a skilled artisan. It should be noted that when a polypeptide of the present invention used in the screening assay has sequences flanking the core amino acid sequence that is at least 90% identical to SEQ ID NO:2 or SEQ ID NO:2 with one or more conservative substitutions, it may be necessary to confirm that an agent binds to the core amino acid sequence rather than the flanking sequences, which can be readily accomplished by a skilled artisan.

B. Biological Activity Assay

In another aspect, the present invention relates to screening assays employing the mSCD4 gene and/or protein for identifying agents that can modulate mSCD4 expression or enzymatic activity. In general, a screening method involves providing a preparation that contains mSCD4 biological activity, contacting the preparation with a test agent, measuring mSCD4 biological activity, and comparing the activity to that of a control preparation that is not exposed to the test agent wherein a higher or lower than control activity indicates that the agent can modulate mSCD4 biological activity. In one embodiment, the method involves administering a test agent to a mouse and determining the effect of the agent on the mSCD4 biological activity in the heart tissue. In one approach, the mSCD4 biological activity is measured by the level of monounsaturated fatty acids, triglycerides, or both in the heart tissue.

1. "Mouse SCD4 Biological Activity"

"Mouse SCD4 biological activity" as used herein, especially relating to screening assays, is interpreted broadly and contemplates all directly or indirectly measurable and identifiable biological activities of the mSCD4 gene and protein.

Relating to the purified mSCD4 protein, mSCD4 biological activity includes, but is not limited to, all those biological processes, interactions, binding behavior, binding-activity relationships, pKa, pD, enzyme kinetics, stability, and functional assessments of the protein. Relating to mSCD4 biological activity in cell fractions, reconstituted cell fractions or whole cells, these activities include, but are not limited to the rate at which the SCD introduces a cis-double bond in its substrates such as palmitoyl-CoA (16:0) and stearoyl-CoA (18:0), which are converted to palmitoleoyl-CoA (16:1) and oleoyl-CoA (18:1), respectively, and all measurable consequences of this effect, such as triglyceride, cholesterol or other lipid synthesis, membrane composition and behavior, cell growth, development or behavior, and other direct or indirect effects of mSCD4 activity. Relating to mSCD4 gene and transcription, mSCD4 biological activity includes the rate, scale or scope of transcription of genomic DNA to generate RNA, the effect of regulatory proteins on such transcription, the effect of modulators of such regulatory proteins on such transcription, and the stability and behavior of mRNA transcripts, post-transcription processing, MRNA amounts and turnover, and all measurements of translation of the MRNA into polypeptide sequences. Relating to mSCD4 biological activity in organisms, this includes but is not limited to biological activities which are identified by their absence or deficiency in disease processes or disorders caused by aberrant mSCD4 biological activity in those organisms. Broadly speaking, mSCD4 biological activity can be determined by all these and other means for analyzing biological properties of proteins and genes that are known in the art.

2. Design and Development of SCD Screening Assays

The present disclosure facilitates the development of screening assays that may be cell based, cell extract (e.g. microsomal assays) or cell free (e.g. transcriptional) assays, and assays of substantially purified protein activity. Such assays are typically radioactivity or fluorescence based (e.g. fluorescence polarization or fluorescence resonance energy transfer (FRET)), or they may measure cell behavior (viability, growth, activity, shape, membrane fluidity, temperature sensitivity etc). Alternatively, screening may employ multicellular organisms, including genetically modified organisms such as knock-out or knock-in (transgenic) mice, or naturally occurring genetic variants. Screening assays may be manual or low throughput assays, or they may be high throughput screens which are mechanically/robotically enhanced.

The aforementioned processes afford the basis for screening processes, including high throughput screening processes, for determining the efficacy of potential agents for modulating mSCD4 activity.

The assays disclosed herein essentially require the measurement, directly or indirectly, of an mSCD4 biological activity. Those skilled in the art can develop such assays based on well known models, and many potential assays exist. For measuring whole cell activity of mSCD4 directly, methods that can be used to quantitatively measure SCD activity include for example, measuring thin layer chromatographs of SCD reaction products over time. This method and other methods suitable for measuring SCD activity are well known (Henderson Henderson R. J., et al. (1992) *Lipid Analysis: A Practical Approach*, Hamilton S. Eds. New York and Tokyo, Oxford University Press. pp 65-111). Gas chromatography is also useful to distinguish monounsaturates from saturates. These techniques can be used to determine if a test compound has influenced the biological activity of mSCD4, or the rate at which the SCD introduces a cis-double bond in its substrates such as palmitoyl-CoA (16:0) and stearoyl-CoA (18:0) to produce palmitoleoyl-CoA (16:1) or oleoyl-CoA (18:1), respectively.

In one embodiment of an mSCD4 activity assay, the assay employs a microsomal assay having a measurable mSCD4 biological activity. A suitable assay may be taken with mouse heart tissue and mSCD4 substrates by modifying and scaling up the rat liver microsomal assay essentially as described by Shimomura et al. (Shimomura, I. et al. (1998) *J. Biol. Chem.* 273, 35299-306). Tissues are homogenized in 10 vol. of buffer A (0.1 M potassium buffer, pH 7.4). The microsomal membrane fractions (100,000×g pellet) are isolated by sequential centrifugation. Reactions are performed at 37° C. for 5 min with 100 μg of protein homogenate and 60 μM of [$^{14}$C]-saturated fatty acyl-CoA (60,000 dpm), 2 mM of NADH, 0.1 M of Tris/HCl buffer (pH 7.2). After the reaction, fatty acids are extracted and then methylated with 10% acetic chloride/methanol. Saturated fatty acid and monounsaturated fatty acid methyl esters are separated by 10% $AgNO_3$-impregnated TLC using hexane/diethyl ether (9:1) as developing solution. The plates are sprayed with 0.2% 2',7'-dichlorofluorescein in 95% ethanol and the lipids are identified under UV light. The fractions are scraped off the plate, and the radioactivity is measured using a liquid scintillation counter.

Specific embodiments of such mSCD4 biological activity assay take advantage of the fact that the SCD reaction produces, in addition to the monounsaturated fatty acyl-CoA product, $H_2O$. If $^3H$ is introduced into the C-9 and C-10 positions of the fatty-acyl-CoA substrate, then some of the radioactive protons from this reaction will end up in water. Thus, the measurement of the activity would involve the measurement of radioactive water. In order to separate the labeled water from the saturated fatty acyl-CoA, investigators may employ substrates such as charcoal, hydrophobic beads, or just plain old-fashioned solvents in acid pH.

In particular, the assay makes use of a $^3H$-saturated fatty acyl-CoA (with the $^3H$ on the 9 and 10 carbon atoms). Desaturation by mSCD4 produces monounsaturated fatty acyl-CoA and $^3H$-water molecules. The reaction is run at room temperature, quenched with acid and then activated charcoal is used to separate unreacted substrate from the radioactive water product. The charcoal is sedimented and amount of radioactivity in the supernatant is determined by liquid scintillation counting. This assay is specific for mSCD4-dependent desaturation as judged by the difference seen when comparing the activity in wild type and SCD4-knockout tissues. Further, the method is easily adapted to high throughput as it is cell-free, conducted at room temperature and is relatively brief (1 hour reaction time period versus previous period of 2 days).

While the instant disclosure sets forth an effective working embodiment of the invention, those skilled in the art are able to optimize the assay in a variety of ways, all of which are encompassed by the invention. For example, charcoal is very efficient (>98%) at removing the unused portion of the saturated fatty acyl-CoA but has the disadvantage of being messy and under some conditions difficult to pipette. It may not be necessary to use charcoal if the saturated fatty acyl-CoA complex sufficiently aggregates when acidified and spun under moderate g force. This can be tested by measuring the signal/noise ratio with and without charcoal following a desaturation reaction. There are also other reagents that would efficiently sediment saturated fatty acyl-CoA to separate it from the $^3H$-water product.

In another embodiment, screening assays measure mSCD4 biological activity indirectly. Standard high-throughput screening assays center on ligand-receptor assays. These may be fluorescence based or luminescence based or radiolabel detection. Enzyme immunoassays can be run on a wide variety of formats for identifying compounds that interact with mSCD4 protein. These assays may employ prompt fluorescence or time-resolved fluorescence immunoassays which are well known. $^{32}$p labeled ATP is typically used for protein kinase assays. Phosphorylated products may be separated for counting by a variety of methods. Scintillation proximity assay technology is an enhanced method of radiolabel assay. All these types of assays are particularly appropriate for assays of compounds that interact with purified or semi-purified mSCD4 protein.

The following assays are also suitable for measuring mSCD4 biological activity in the presence of potential agents. These assays are also valuable as secondary screens to further select mSCD4 specific inhibitors from a library of potential therapeutic agents.

Cellular based desaturation assays can be used to track mSCD4 activity levels. By tracking the conversion of saturated fatty acyl-CoA to monounsaturated fatty acyl-CoA in cells (e.g., mouse heart cells) one can evaluate compounds found to be modulators in the primary screen for additional qualities or characteristics such as whether they are cell permeable, lethal to cells, and/or competent to inhibit or increase mSCD4 activity in cells. This cellular based assay may employ a recombinant cell line containing mSCD4. The recombinant gene is optionally under control of an inducible promoter and the cell line preferably over-expresses mSCD4 protein.

Other assays for tracking other SCD isoforms can be developed. For example, mSCD1 and mSCD2 microsomal preparations can be made from mouse liver and brain, respectively. The object may be to find compounds that would be specific to mSCD4. This screen would compare the inhibitory or enhancing effect of the compound for mSCD4 versus mSCD1 and mSCD2.

Cell based assays may be preferred, for they leave the mSCD4 gene in its native format. Particularly promising for mSCD4 analysis in these types of assays are fluorescence polarization assays. The extent to which light remains polarized depends on the degree to which the tag has rotated in the time interval between excitation and emission. Since the measurement is sensitive to the tumbling rate of molecules, it can be used to measure changes in membrane fluidity characteristics that are induced by mSCD4 activity—namely the delta-9 desaturation activity of the cell. An alternate assay for mSCD4 involves a FRET assay. FRET assays measure fluorescence resonance energy transfer which occurs between a fluorescent molecule donor and an acceptor, or quencher. Such an assay may be suitable to measure changes in membrane fluidity or temperature sensitivity characteristics induced by mSCD4 biological activity.

The screening assays of the invention may be conducted using high throughput robotic systems. In the future, preferred assays may include chip devices developed by, among others, Caliper, Inc., ACLARA BioSciences, Cellomics, Inc., Aurora Biosciences Inc., and others.

In other embodiments of an mSCD4 assay, mSCD4 biological activity can also be measured through a cholesterol efflux assay that measures the ability of cells to transfer cholesterol to an extracellular acceptor molecule and is dependent on ABCA1 function. A standard cholesterol efflux assay is set out in Marcil et al. (1999) *Arterioscler. Thromb. Vasco Bioi.* 19, 159-169, incorporated herein by reference in its entirety.

Preferred assays are readily adapted to the format used for drug screening, which may consist of a multi-well (e.g., 96-well, 384 well or 1,536 well or greater) format. Modification of the assay to optimize it for drug screening would include scaling down and streamlining the procedure, modifying the labeling method, altering the incubation time, and changing the method of calculating mSCD4 biological activity and so on. In all these cases, the mSCD4 biological activity assay remains conceptually the same, though experimental modifications may be made.

Another preferred cell based assay is a cell viability assay for the isolation of mSCD4 inhibitors. Overexpression of mSCD4 is expected to decrease cell viability. This expected phenotype can be exploited to identify inhibitory compounds. This cytotoxicity may be due to alteration of the fatty acid composition of the plasma membrane. In a preferred embodiment, the mSCD4 cDNA would be placed under the control of an inducible promoter, such as the Tet-On Tet-Off inducible gene expression system (Clontech). This system involves making a double stable cell line. The first transfection introduces a regulator plasmid and the second would introduce the inducible mSCD4 expression construct. The chromosomal integration of both constructs into the host genome would be favored by placing the transfected cells under selective pressure in the presence of the appropriate antibiotic. Once the double stable cell line was established, mSCD4 expression would be induced using the tetracycline or a tetracycline derivative (e.g., Doxycycline). Once mSCD4 expression had been induced, the cells would be exposed to a library of chemical compounds for high throughput screen of potential inhibitors. After a defined time period, cell viability would then be measured by means of a fluorescent dye or other approach (e.g., turbidity of the tissue culture media). Those cells exposed to compounds that act to inhibit mSCD4 activity would show increased viability, above background survival. Thus, such an assay would be a positive selection for inhibitors of mSCD4 activity based on inducible mSCD4 expression and measurement of cell viability.

An alternative approach is to assay SCD activity is to measure the interference of the desaturase system. As described earlier, the desaturase system has three major proteins: cytochrome $b_5$, NADH (P)-cytochrome $b_5$ reductase, and terminal cyanide-sensitive desaturase. Terminal cyanide-sensitive desaturase is the product of the SCD gene. SCD activity depends upon the formation of a stable complex between the three aforementioned components. Thus, any agent that interferes with the formation of this complex or any agent that interferes with the proper function of any of the three components of the complex would effectively inhibit SCD activity.

An mSCD4 activity assay may also be carried out as a cell free assay employing a cellular fraction, such as a microsomal fraction, obtained by conventional methods of differential cellular fractionation, most commonly by ultracentrifugation methods.

When any agent is tested in animals including humans, SCD biological activity can be measured indirectly by the ratio of monounsaturated to saturated fatty acids (correspond to a monounsaturated fatty acyl-CoA product and saturated fatty acyl-CoA substrate, respectively) in the total plasma lipid fraction.

3. Mouse SCD4-Containing Genetic Constructs and Recombinant Cells that can be Used for mSCD4 Production and Screening Assays In certain embodiments, screening protocols contemplate use of the mSCD4 gene or protein in genetic constructs or recombinant cells or cell lines, some of which have been described above. Mouse SCD4 recombinant cells and cell lines may be generated using techniques known in the art, and those more specifically set out below.

Genetic constructs (e.g., vectors) which contain the mSCD4 gene can be generated and introduced into host cells, especially where such cells result in a cell line that can be used for assay of mSCD4 activity, and production of mSCD4 polypeptides by recombinant techniques.

The host cell can be a higher eukaryotic cell, such as a mammalian cell or an insect cell (e.g., SF9 cells from *Spodoptera frugiperda*), or a lower eukaryotic cell, such as a yeast cell, or the host cell can be a prokaryotic cell, such as a bacterial cell. The selection of an appropriate host is deemed to be within the knowledge of those skilled in the art based on the teachings herein. Host cells are genetically engineered (transduced or transformed or transfected) with the vectors which may be, for example, a cloning vector or an expression vector. The engineered host cells are cultured in conventional nutrient media modified as appropriate for activating promoters, selecting transformants or amplifying the mSCD4 gene. The culture conditions, such as temperature, pH and the like, are those previously used with the host cell selected for expression, and will be apparent to a skilled artisan.

It is well within the knowledge and skill of a skilled artisan to construct a genetic construct or vector containing the mSCD4 gene that can be used to express mSCD4 at the MRNA or protein level in a cell or cell-free system. Such constructs or vectors may include chromosomal, nonchromosomal and synthetic DNA sequences, e.g., derivatives of SV40, bacterial plasmids, phage DNA, baculovirus, yeast plasmids, vectors derived from combinations of plasmids and phage DNA, viral DNA such as vaccinia, adenovirus, fowl pox virus, and pseudorabies. Appropriate cloning and expression vectors for use with prokaryotic and eukaryotic hosts are described by Sambrook, et al., *Molecular Cloning: A laboratory Manual*, Second Edition, Cold Spring Harbor, N.Y., (1989), Wu et al., *Methods in Gene Biotechnology* (CRC Press, New York, N.Y., 1997), Recombinant Gene Expression Protocols, In Methods in Molecular Biology, Vol. 62, (Tuan, ed., Humana Press, Totowa, N.J., 1997), and *Current Protocols in Molecular Biology*, (Ausabel et al., Eds.,), John Wiley & Sons, NY (1994-1999), the disclosures of which are hereby incorporated by reference in their entirety. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may also be used as long as they can express mSCD4 under suitable conditions.

The appropriate polynucleotide sequence may be inserted into the vector by a variety of procedures. In general, the polynucleotide sequence is inserted into an appropriate restriction endonuclease site(s) by procedures known in the art. Such procedures and others are deemed to be within the scope of those skilled in the art.

The polynucleotide sequence in an expression vector is operatively linked to an appropriate expression control sequence(s) (e.g., promoter) to direct mRNA synthesis. Representative examples of such promoters include bacterial promoters such as lacl, lacZ, T3, T7, gpt, lambda $P_R$, $P_L$, and trp and eukaryotic promoters such as CMV immediate early, HSV thymidine kinase, early and late SV40, LTRs from retrovirus, and mouse metallothionein-I. Other promoters known to control expression of genes in prokaryotic or eukaryotic cells or their viruses can also be used. Selection of the appropriate vector and promoter is well within the level of ordinary skill in the art. The expression vector may contain a ribosome binding site for translation initiation and a transcription terminator. The vector may also include appropriate sequences for amplifying expression.

In addition, an expression vector preferably contains one or more selectable marker genes to provide a phenotypic trait for selection of transformed host cells such as dihydrofolate reductase or neomycin resistance for eukaryotic cell culture or such as tetracycline or ampicillin resistance in *E. coli*.

Transcription of the DNA encoding the mSCD4 protein by eukaryotic cells, especially mammalian cells, most especially mouse or human cells, can be increased by inserting an enhancer sequence into the expression vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Optionally, a leader sequence capable of directing secretion of translated protein into the periplasmic space or extracellular medium can be included in the expression vector to facilitate downstream applications of the protein generated. Further, extra nucleotide sequences can be added to a mSCD4 coding sequence in the expression vector for producing a mSCD4 fusion protein that includes an N-terminal or C-terminal identification peptide imparting desired characteristics, e.g., stabilization or simplified purification of expressed recombinant product.

A baculovirus-based expression system is especially useful for expressing mSCD4 as disclosed herein. Baculoviruses represent a large family of DNA viruses that infect mostly insects. The prototype is the nuclear polyhedrosis virus (AcMNPV) from *Autographa californica*, which infects a number of lepidopteran species. One advantage of the baculovirus system is that recombinant baculoviruses can be produced in vivo. Following co-transfection with transfer plasmid, most progeny tend to be wild type and a good deal of the subsequent processing involves screening. To help identify plaques, special systems are available that utilize deletion mutants. By way of non-limiting example, a recombinant AcMNPV derivative (called BacPAK6) has been reported in the literature that includes target sites for the restriction nuclease Bsu361 upstream of the polyhedrin gene (and within ORF 1629) that encodes a capsid gene (essential for virus viability). Bsf361 does not cut elsewhere in the genome and digestion of the BacPAK6 deletes a portion of the ORF1629, thereby rendering the virus nonviable. Thus, with a protocol involving a system like Bsu361-cut BacPAK6 DNA most of the progeny are nonviable so that the only progeny obtained after co-transfection of transfer plasmid and digested BacPAK6 is the recombinant because the transfer plasmid, containing the exogenous DNA, is inserted at the Bsu361 site thereby rendering the recombinants resistant to the enzyme (see Kitts and Possee (1993) A method for producing baculovirus expression vectors at high frequency, *BioTechniques,* 14, 810-817). For general procedures, see King and Possee, The Baculovirus Expression System: A Laboratory Guide, Chapman and Hall, New York (1992) and Recombinant Gene Expression Protocols, in Methods in Molecular Biology, Vol. 62, (Tuan, ed., Humana Press, Totowa, N.J., 1997), at Chapter 19, pp. 235-246.

It is understood that a vector construct comprising a SCD4 promoter sequence (e.g., SEQ ID NO:3 or a functional fragment thereof) operably linked to a reporter gene as disclosed herein can be used to study the effect of potential transcription regulatory proteins, and the effect of compounds that inhibit or enhance the effect of those regulatory proteins, on the transcription of mSCD4.

Factors that may modulate gene expression can be readily identified by a skilled artisan from the mSCD4 promoter sequence provided herein (SEQ ID NO:3). Screening assays designed to assess the capacity of test compounds to inhibit or enhance the ability of these transcription factors to transcribe mSCD4 are contemplated by this invention.

4. Test Compounds/Inhibitors/Enhancers/Library Sources

In accordance with the foregoing, the present invention also relates to agents, regardless of molecular size or weight, effective in inhibiting or enhancing the activity and/or expression of mSCD4, and most preferably where said agents have been determined to have such activity through at least one of the screening assays disclosed according to the present invention.

Test compounds are generally compiled into libraries of such compounds and a key object of the screening assays of the invention is to select which compounds are relevant from libraries having hundreds of thousands or millions of compounds.

Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic-, or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

Thus, in one aspect the present invention relates to agents capable of inhibiting or enhancing the activity and/or expression of mSCD4, especially where said inhibiting or enhancing ability was first determined using an assay involving the use of mSCD4 protein or mSCD4 gene or an assay which measures mSCD4 activity. As used herein the term "capable of inhibiting or enhancing" refers to the characteristic of such an agent whereby said agent has the effect of inhibiting or enhancing the overall biological activity of mSCD4, either by decreasing or increasing said activity, under suitable conditions of temperature, pressure, pH and the like so as to facilitate such inhibition or enhancement to a point where it can be detected either qualitatively or quantitatively and wherein such inhibition or enhancement may occur in either an in vitro or in vivo environment. In addition, while the term "inhibition" or "enhancement" is used herein to mean a decrease or increase in activity, the term "activity" is not to be limited to specific enzymatic activity alone (for example, as measured in units per milligram or some other suitable unit of specific activity) but includes other direct and indirect effects of the protein, including decreases or increases in enzyme activity due not to changes in specific enzyme activity but due to changes of expression of polynucleotides encoding and expressing said mSCD4 enzyme. The term "inhibition" or "enhancement" as used herein means a decrease or increase in mSCD4 activity regardless of the molecular or genetic level of said inhibition or enhancement, be it an effect on the enzyme per se or an effect on the genes encoding the enzyme or on the RNA, especially mRNA, involved in expression of the genes encoding said enzyme. Thus, modulation by such agents can occur at the level of DNA, RNA or enzyme protein and can be determined either in vivo or ex vivo.

In specific embodiments thereof, said assay is any of the assays disclosed herein according to the invention. In addition, the agent(s) contemplated by the present disclosure includes agents of any size or chemical character, either large or small molecules, including proteins, such as antibodies, nucleic acids, either RNA or DNA, and small chemical structures, such as small organic molecules.

5. Combinatorial and Medicinal Chemistry

Typically, a screening assay, such as a high throughput screening assay, will identify several or even many compounds which modulate the activity of the assay protein. A compound identified by the screening assay may be further modified before it is used in animals as a therapeutic agent. Typically, combinatorial chemistry is performed on the inhibitor or enhancer, to identify possible variants that have improved absorption, biodistribution, metabolism and/or excretion, or other important aspects. The essential invariant is that the improved compounds share a particular active group or groups which are necessary for the desired inhibition or enhancement of the target protein. Many combinatorial chemistry and medicinal chemistry techniques are well known in the art. Each one adds or deletes one or more constituent moieties of the compound to generate a modified analog, which analog is again assayed to identify compounds of the invention. Thus, as used in this invention, compounds identified using a mSCD4 screening assay of the invention include actual compounds so identified, and any analogs or combinatorial modifications made to a compound which is so identified which are useful for inhibiting or enhancing mSCD4 activity.

V. Pharmaceutical Preparations and Dosages

In another aspect the present invention is directed to compositions comprising the polynucleotides, polypeptides or other chemical agents, including therapeutic or prophylactic agents, such as small organic molecules, disclosed herein according to the present invention wherein said polynucleotides, polypeptides or other agents are suspended in a pharmacologically acceptable carrier, which carrier includes any pharmacologically acceptable diluent or excipient. Pharmaceutically acceptable carriers include, but are not limited to, liquids such as water, saline, glycerol and ethanol, and the like. A thorough discussion of pharmaceutically acceptable carriers, diluents, and other excipients is presented in Remington's Pharmaceutical Sciences (Mack Pub. Co., N.J, current edition), which is herein incorporated by reference in its entirety.

The mSCD4 inhibitors or enhancers utilized above may be delivered to a subject using any of the commonly used delivery systems known in the art, as appropriate for the inhibitor or enhancer chosen. The preferred delivery systems include intravenous injection or oral delivery, depending on the ability of the selected inhibitor or enhancer to be adsorbed in the digestive tract. Any other delivery system appropriate for delivery of small molecules, such as skin patches, may also be used as appropriate.

VI. Diagnosis

In an additional aspect, the present invention also relates to a process for diagnosing a disease or condition in an animal (e.g., mouse and human) being suspected of being afflicted therewith or at risk of becoming afflicted therewith, comprising obtaining a tissue sample (e.g., a heart tissue sample) from said animal and determining the level of activity of SCD4 (e.g., mSCD4 and its human counterpart) in the cells of said tissue sample and comparing said activity to that of an equal amount of the corresponding tissue from an animal not suspected of being afflicted with or at risk of becoming afflicted with said disease or condition. In specific embodiments thereof, said disease or condition includes, but is not limited to, fatty heart.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

In applying the disclosure, it should be kept clearly in mind that other and different embodiments of the compositions and methods disclosed according to the present invention will no doubt suggest themselves to those of skill in the relevant art.

The invention will be more fully understood upon consideration of the following non-limiting example.

EXAMPLE

Identification and Characterization of Murine SCD4, a Novel Heart-Specific SCD Isoform Regulated by Leptin and Dietary Factors SCD is the rate-limiting enzyme in the biosynthesis of monounsaturated fatty acids. Thus far, three isoforms of SCD (mSCD1, mSCD2, and mSCD3) have been identified and characterized in mice. This example shows the cDNA cloning and characterization of a fourth mouse SCD isoform (mSCD4) that is expressed predominantly in the heart. Mouse SCD4 encodes a 353-amino acid protein that shares 79% sequence identity with the mSCD1, mSCD2, and mSCD3 isoforms. Liver X receptor α (LXR α) agonists and a high carbohydrate fat-free diet induced mSCD4 expression, but unlike mSCD1, mSCD4 expression was not repressed by dietary polyunsaturated fatty acids. Mouse SCD4 mRNA levels were elevated 5-fold in the hearts of leptin-deficient ob/ob mice relative to wild type controls. Treatment of ob/ob mice with leptin decreased MRNA levels of mSCD4, whereas levels of mSCD1 and mSCD2 were not affected. Furthermore, in the hearts of SCD1-deficient mice, mSCD4 MRNA levels were induced 3-fold, whereas the levels of mSCD2 were not altered.

Experimental Procedures

Animals and Diets—Male C57BL6J and ob/ob mice were obtained from the Jackson Laboratory (Bar Harbor, Me.). 129S6/SvEv mice were purchased from Taconic (Germantown, N.Y.). The mice (14-16 weeks old) were maintained on a 12-h dark/light cycle and were fed a normal nonpurified diet (5008 test diet; PMI Nutrition International Inc., Richmond, Ind.), a high carbohydrate fat-free diet (TD99252, Harlan Teklad, Madison, Wis.), or high carbohydrate fat-free diet supplemented with fish oil. In some experiments the chow diet was supplemented with 0.025% T0901317, an LXRα agonist (Cayman, Ann Arbor, Mich.), which was fed to the mice for 2 days. All animal breeding was in accordance with protocols approved by the animal care research committee of the University of Wisconsin-Madison.

Materials—Radioactive [$^{32}$P]dCTP (3000 Ci/mmol) was obtained from DuPont. Thin layer chromatography plates (TLC Silica Gel G60) were from Merck. [$^{14}$C]Stearoyl-CoA and [$^{14}$C]palmitoyl-CoA were obtained from American Radiolabeled Chemicals Inc. (St. Louis, Mo.). The cDNA probes for mSCD1 and mSCD2 are as described in Gomez, F. E. et al. (2002) *Biochemistry* 41, 5473-5482, which is herein incorporated by reference in its entirety. All other chemicals were purchased from Sigma.

Subcutaneous Leptin Treatment—ob/ob mice were individually caged and allowed to acclimate for a number of days prior to the start of the experiment. The mice were treated with 200 ng/h of recombinant mouse leptin (Amgen, Thousand Oaks, Calif.) and phosphate-buffered saline (PBS) for 12 days using subcutaneously placed Alzet miniosmotic pumps model 1002 (AlZa Co., Palo Alto, Calif.) as described in Soukas, A. et al. (2000) *Genes Dev.* 14, 963-980, which is herein incorporated by reference in its entirety. As an additional control, a group of mice referred to as pair-fed was treated with PBS and given the same amount of food to eat as leptin-treated mice voluntarily consumed. All of the data presented were generated from this or a similar time course where mice were either treated with PBS or leptin for 12 days. Body mass and food intake were measured daily.

Isolation and Analysis of RNA—Total RNA was extracted from the hearts of 5 ob/ob male C57BL6 and SCD1-/- mice as well as the appropriate wild type controls using Trizol reagent (Invitrogen) (Miyazaki, M. et al. (2002) *J. Lipid Res.* 43, 2146-2154). For Northern blot analysis, 15 μg of total RNA were separated by 1.0% agarose, 2.2 M formaldehyde gel electrophoresis and transferred onto a nylon membrane. The membrane was hybridized with $^{32}$P-labeled cDNA probes.

Cloning and Expression of the Mouse SCD4 cDNA—A BLAST search of the mouse genomic data base identified a gene with exon sequences highly homologous to the amino acid sequence of mouse SCD1, 2, and 3 (GenBank™ accession numbers AH_002082, M26270, and AF272037, respectively). Using the genomic sequence, a candidate open reading frame of the putative SCD4 was cloned by synthesizing a forward and a reverse primer. The primers were utilized to screen total RNA isolated from the hearts of SCD1-/- mice by PCR amplification. The amplification conditions consisted of an initial denaturation step at 94° C. for 3 min followed by 40 cycles at 94° C. for 30 s, 58° C.

for 1 min, and finally 1 cycle at 72° C. for 10 min. The resulting PCR product was cloned into the T-easy vector (Promega, Madison, Wis.) and sequenced. The construct was named pTA-mSCD4. The 5' upstream and 3' downstream regions of the SCD4 cDNA that were missing from pTA-SCD4 were obtained by a SMART™ RACE (rapid amplification of cDNA ends) kit (Clontech, Palo Alto, Calif.) using the primers 5'-TCCTGCTGTCTCCGG-GAGTGGGGTTCCA-3' (SEQ ID NO:4) and 5'-TTGGC-CAACCTCCCCAAGGCTTCACAGC-3' (SEQ ID NO:5), respectively. The 5'-RACE and 3'-RACE products were cloned in the T-easy vector and then sequenced. The complete SCD4 cDNA was then obtained using the forward primer (5'-ACAGCAGAACTGACTGGTGACACCTGCA-CAGTTAG-3' (SEQ ID NO:6)) and reverse primer (5'-CCGAGAGCGCTCTTGAATAAAAAAATCCTCTTGC-3' (SEQ ID NO:7)) and then sequenced. A Multiple Tissue Northern blot (Clontech, catalog number 7762-1) was used to detect SCD4 expression in mouse heart, brain, spleen, lung, liver, skeletal muscle, and kidney. The EcoRI-StyI fragment (186 bp) of the 5'-RACE product of SCD4 was used as the probe. It was tested against mSCD1, 2, and 3 there was no cross-hybridization. The specific probes for mSCD1, mSCD2, and mSCD3 derived from the 5'-untranslated region are described in Miyazaki, M. et al. (2001) *J. Biol. Chem.* 276, 39455-39461, which is herein incorporated by reference in its entirety. For additional tissues, RT (reverse transcriptase)-PCR was performed using the mSCD4 primers 5'-AGGATGGAGAAGAGAAGATGCC-3' (forward) (SEQ ID NO:8) and 5'-AGTTGTTTTATGGAACA-GAGACCC-3' (reverse) (SEQ ID NO:9). Mouse SCD4 primers for quantitative RT-PCR are 5'-GCTCTCTCTGC-CTTCACAAGA-3' (forward) (SEQ ID NO:10) and 5'-TGT-TCCTCCAGACGTACTCCAGCTT-3' (reverse) (SEQ ID NO:11). Realtime quantitative PCR using mSCD1-, mSCD2-, mSCD3-, cyclophilin-, and glyceraldehyde-3-phosphate dehydrogenase-specific primers was performed as described in Miyazaki, M. et al. (2002) *J. Lipid Res.* 43, 2146-2154, which is herein incorporated by reference in its entirety.

To introduce an N-terminal hemagglutinin (HA) epitope tag into the cytomegalovirus promoter of the pcDNA3 expression vector (Invitrogen), PCR was performed with pTA-mSCD4 as the template, using a forward primer (TTGAATTCACCATGTACCCATAT-GACGTCCCGGACTACGCCATGACGGCCCACTT GCCAC (SEQ ID NO:12)) and a reverse primer (5'-TTGCTCGAGTCAGCTACTCTTGTGACTCCC-3' (SEQ ID NO: 13)). The EcoRI-XhoI fragment of the PCR product was ligated into pcDNA3, and the construct was named pcDNA3-HAmSCD4. HEK-293 (ATCC) cells were plated on 10-cm plates in medium supplemented with 10% fetal bovine serum, 100 units/ml penicillin G sodium, and 100 µg/ml streptomycin sulfate. After 24 h, at 80-90% confluence, the cells were transfected with 10 µg of SCD4 expression vector or pcDNA3, using 60 µl of SuperFect transfection reagent (Qiagen). 36 h after transfection, the cells were harvested, and the microsomes were isolated. Expression of HA-tagged mSCD4 protein in microsomes was determined by immunoblot analysis. Microsomal protein (10 µg) was electrophoresed on an 8% SDS-PAGE and transferred to a nitrocellulose membrane (Millipore, Bedford, Mass.). The membrane was blocked at room temperature for 1 h in Tris-buffered saline containing 1% bovine serum albumin and then incubated with 100 ng/ml anti-HA monoclonal antibody (clone 3F10; Roche Applied Science) in Tris-buffered saline containing 1% bovine serum albumin for 1 h at room temperature. After washing with Tris-buffered saline containing 0.1% Tween 20, the membrane was incubated with horseradish peroxidase-conjugated anti-rat IgG at a 1:20000 dilution (Sigma) for 30 min at room temperature. Visualization was performed with an ECL Western blot detection kit (Amersham Biosciences).

Enzyme Assays—Microsomes were isolated from hearts of ob/ob mice as well as from HEK-293 cells by differential centrifugation and suspended in a 0.1 M potassium phosphate buffer (pH 7.2). SCD activity was assayed at 23° C. with 3 µM [$^{14}$C]stearoyl-CoA or [$^{14}$C]palmitoyl-CoA, 2 mM NADH, and 100 µg of microsomal protein. After 5 min of incubation, 200 µl of 2.5 M KOH in 75% ethanol was added, and the reaction mixture was saponified at 85° C. for 1 h. The samples were cooled and acidified with 280 µl of formic acid. Free fatty acids were extracted with 700 µl of hexane and separated on a 10% $AgNO_3$-impregnated TLC plate using chloroform:methanol:acetic acid: $H_2O$ (90:8:1:0.8). The TLC plates were analyzed with Instant Imager (Packard, Meriden, Conn.) overnight.

Fatty Acid Analysis—Total lipids were extracted from the hearts or HEK cells according to the method of Bligh and Dyer as described in Miyazaki, M. et al. (2002) *J. Lipid Res.* 43, 2146-2154. The fatty acids were quantitated by gas-liquid chromatography (GLC) as described in Miyazaki, M. et al. (2001) *J. Biol. Chem.* 276, 39455-39461. Pentadecanoic acid (Sigma) was added as an internal standard for the quantitation of fatty acids.

Results

FIG. 1 shows a Northern blot of total RNA isolated from hearts of ob/ob mice and wild type controls measuring the levels of mSCD1 and mSCD2. Mouse SCD1 and SCD2 mRNA levels were similar between wild type and ob/ob mice (FIG. 1, A and B). However, the SCD activity (FIG. 1C) and levels of C16:1 and C18:1 monounsaturated fatty acids, the SCD products, were significantly elevated in ob/ob hearts (FIG. 1D), which first suggested the presence of another SCD isoform that was induced in the heart by leptin deficiency.

We searched the mouse genomic DNA data base (www-.genomic.ucsc.edu) for other mouse SCD homologues, using the amino acid sequences of other members of the mouse SCD family. A predicted cDNA sequence with a 78-86% similarity to the other SCD isoforms was identified. We designed specific primers for the predicted SCD cDNA and used them in a PCR analysis to screen cDNAs prepared from total RNA isolated from hearts of mice with a targeted disruption in the SCD1 isoform (SCD1−/−). SCD1−/− mice were used to minimize cross-reactivity of the primers with mSCD1 sequences expressed in wild type mice. The PCR product was sequenced, and the missing 5'- and 3'-untranslated region sequences were obtained by 5'- and 3'-RACE. The resulting cDNA had an inframe termination codon 248 nucleotides upstream of the putative methionine initiator codon, suggesting that the entire open reading frame had been obtained, and it was designated SCD4.

The gene structure, predicted amino acid sequence and hydrophobicity plots of the mouse SCD4 cDNA and protein are shown in FIG. 2. The sequence of the gene obtained by BLAST analysis of the mouse genome resources of UCSC as well as sequence from two isolated BAC clones revealed that the mouse SCD4 spans 14 kb and has 6 exons and 5 introns (FIG. 2A). The open reading frame that terminates in exon 6 predicts a 353-amino acid protein with a theoretical molecular mass of 41 kDa sharing approximately 83% nucleotide homology with the other three SCD isoforms.

Amino acid sequence alignment of mSCD4 with mSCD1, mSCD2, and mSCD3 indicates sequence identity of greater than 77% and includes 100% conservation of the three histidine motifs HRLWSH, HRAHH, and HNYHH that exist in other desaturases (FIG. 2B). The hydropathy plot shows that the SCD4 protein possesses four transmembrane domains (FIG. 2C), similar to other SCD isoforms.

Figure 3:
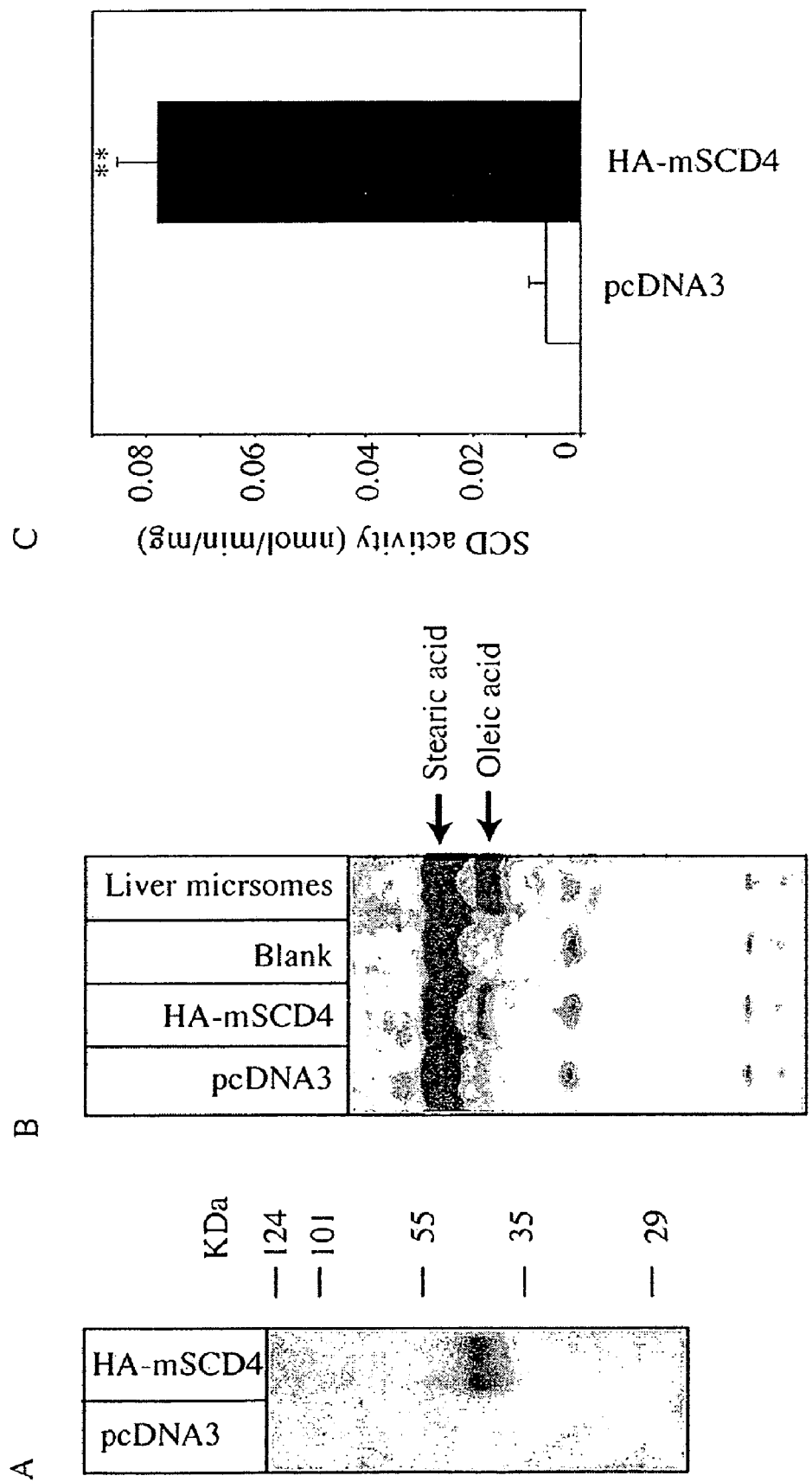
FIG. 3 shows the expression of HA-tagged mSCD4 in membrane fractions of transfected HEK-293 cells. A, Cultured HEK-293 cells were transiently transfected with a HA-tagged SCD4 cDNA expression plasmid (pcDNA3-HA-mSCD4) or the vector alone (pcDNA3). After 48 h the cells were harvested, and the membrane fractions were isolated. Aliquots (30 µg) of membranes were analyzed by SDS-PAGE and immunoblot analysis with 1:500 dilution of an anti-HA monoclonal antibody. The filter was exposed to film for 5 seconds at room temperature. B, SCD enzyme activity: Microsomes were prepared from HEK-293 cells that had been transfected with pcDNA3-HA-SCD4 or pcDNA3 expression vectors, and SCD enzyme activity was determined by measuring the incorporation of radioactivity in oleoyl-CoA using [1-$^{14}$C]stearoyl-CoA as a substrate. Liver microsomes that have a high SCD activity were used as a control. The reaction products were separated by TLC, and the radioactivity was quantitated in C. **, $p<0.001$ versus pcDNA3 (Student's t test).

To determine whether mSCD4 functions as a Δ9-desaturase, HEK-293 cells were transfected with a pcDNA3-HA-tagged SCD4 vector under the control of the cytomegalovirus promoter (pcDNA3-HA-mSCD4). Immunoblot analysis with an HA antibody showed that mSCD4 protein was expressed in the microsomal fractions (FIG. 3A), migrating at a molecular mass of approximately 41 kDa similar to other SCD isoforms. SCD activity was measured in isolated membranes and compared with HEK-293 cells transfected with empty vector alone (pcDNA3). FIG. 3B and the densitometric quantitation (FIG. 3C) shows that SCD activity using 18:0 as a substrate was increased 8-fold in microsomes from pcDNA3-HA-mSCD4 transfected cells compared with cells transfected with empty vector alone (pcDNA3). SCD activity was increased 3-fold when 16:0 was used as substrate. It is expected that 14:0, 15:0, and 17:0 can also serve as substrates for mSCD4.

Figure 4:
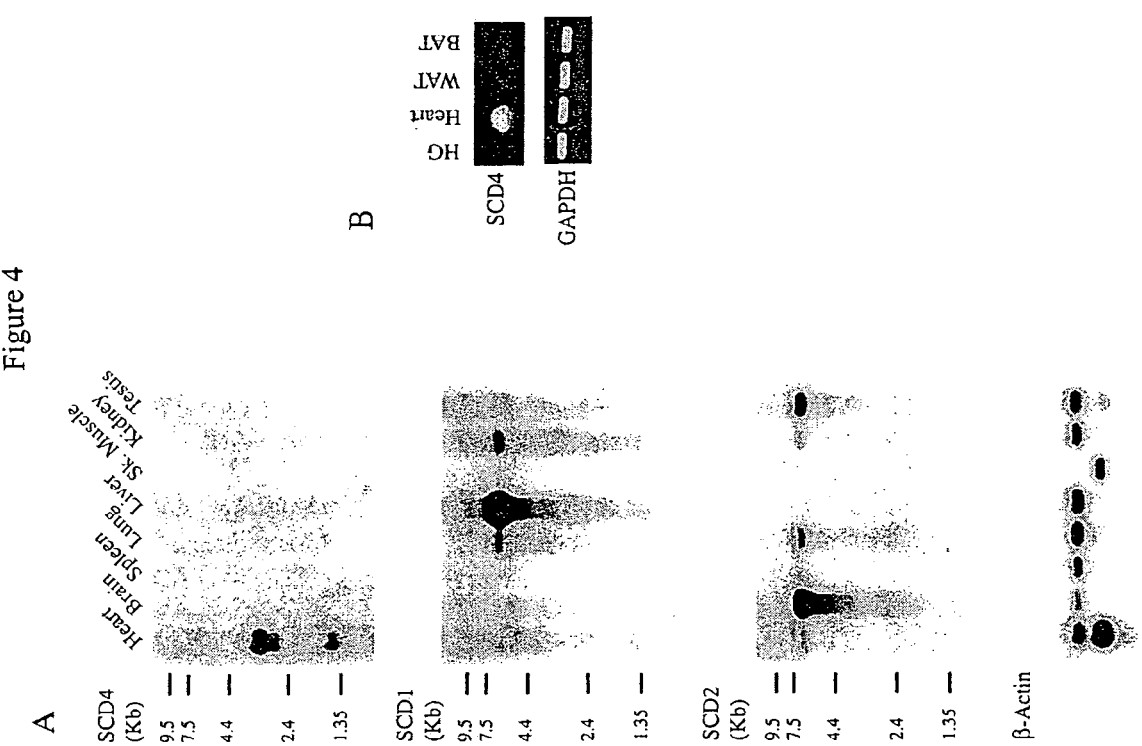
FIG. 4 shows tissue distribution of mSCD4 mRNA. A, Commercial blot containing poly(A$^+$) mRNA from eight mouse tissues were hybridized to $^{32}$P-labeled SCD1-, SCD2-, and SCD4-specific probes as described in the example below. The blots were stripped and rehybridized with a β-actin probe to indicate the presence of mRNA in each lane. A 3.1-kb major transcript and a 1.5-kb minor transcript were detected only in the heart. B, RT-PCR of additional mouse tissues: WAT, white adipose tissue; BAT, brown adipose tissue; HG, Haderian gland.

To determine the tissue expression pattern of mSCD4, a commercially prepared filter (Clontech) containing 2 μg of poly(A$^+$) RNA from several mouse tissues was hybridized with the SCD4-specific probe. Additional RNA isolated from other tissues (brown adipose, white adipose, and Harderian gland) was analyzed by RT-PCR using mSCD4-specific primers. The Northern blot (FIG. 4A) and RT-PCR analysis of additional tissues (FIG. 4B) show that the heart is the only tissue expressing SCD4. Mouse SCD1 is most abundantly expressed in liver, lung, and kidney, whereas mSCD2 is mainly expressed in brain, lung, and testis. Mouse SCD3 was expressed only in the Harderian gland. The 3.1-kb MRNA transcript was the predominant species of mSCD4, with two minor transcripts (2.8 and 1.5) that probably arise from the use of multiple GAAA repeats within exon 6 as cleavage sites for the addition of polyadenylate. The SCD4 MRNA is thus smaller than the 4.9 kb of the other SCD isoforms, because of a shorter 3'-untranslated region.

Figure 5:
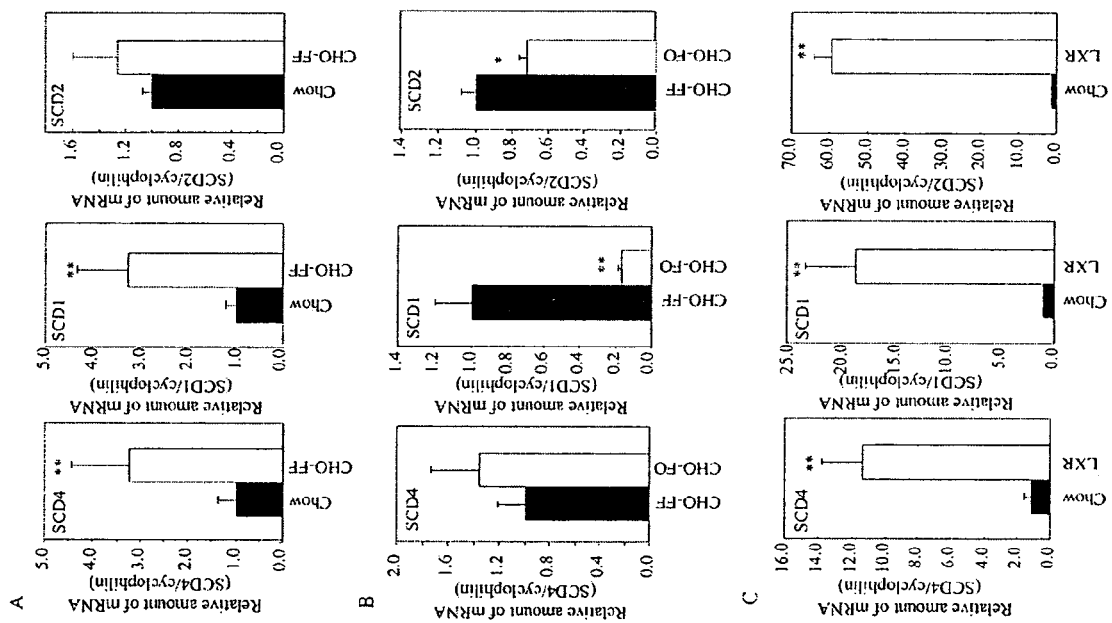
FIG. 5 shows regulation of mSCD4 by high carbohydrate fat-free diet, polyunsaturated fatty acids, and LXRα agonist. The mice were fed the following diets. A, a high carbohydrate fat-free diet (CHO-FF). B, high carbohydrate fat-free diet supplemented with fish oil (CHO-FO) that was fed for 4 days. C, chow diet supplemented with the LXRα agonist T0901317 (LXR) and fed for 2 days. Total RNA from hearts of mice from each group (n=4) was subjected to quantitative RT-PCR using specific primers as described in the example below. The fold change was calculated after correction for the levels of cyclophilin used as a standard. Each value represents the mean±S.E. (n=4). *, $p<0.01$; **, $p<0.001$ versus wild type (Student's t test).
Figure 6:
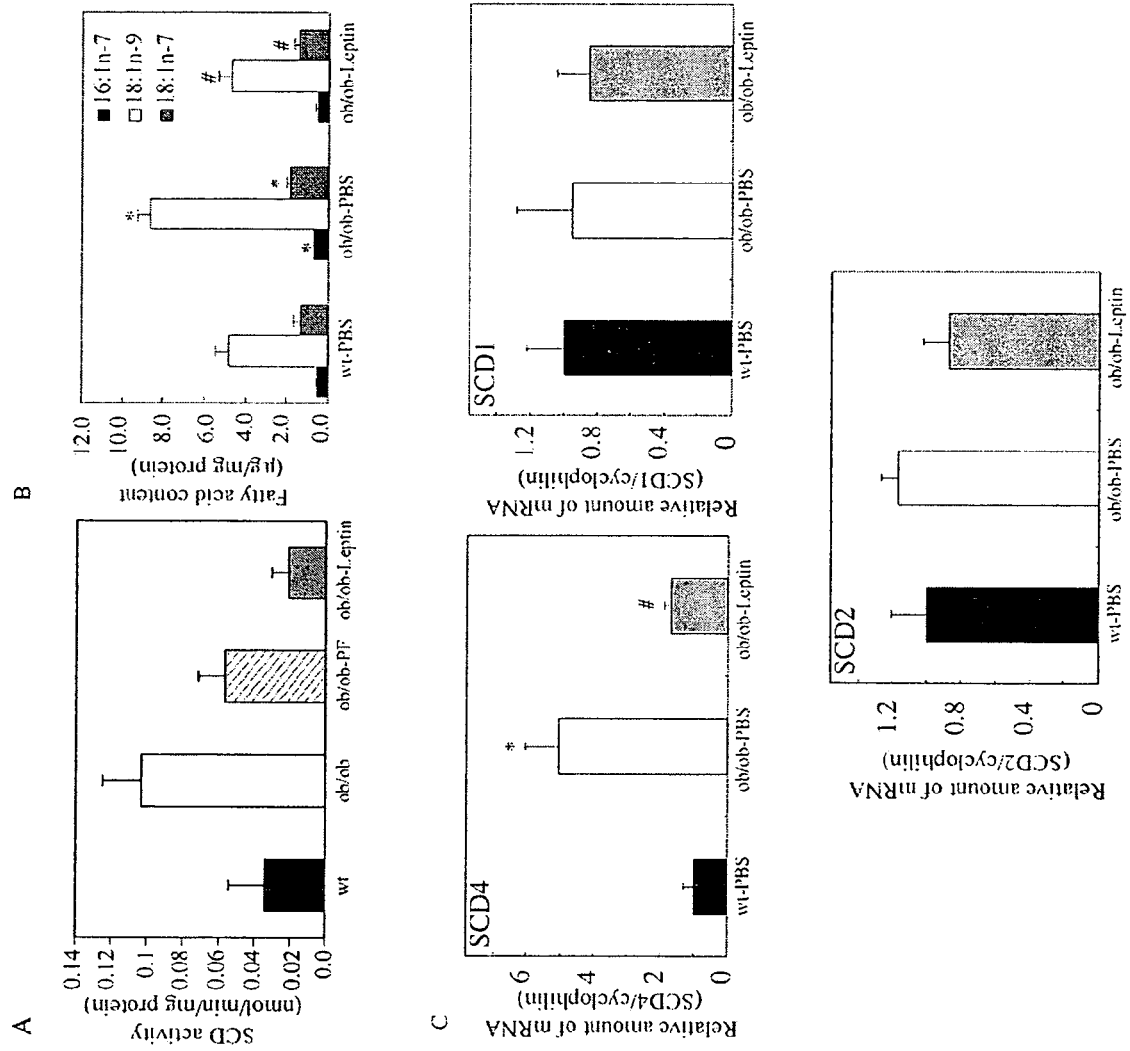
FIG. 6 shows regulation of mSCD4 by leptin. A, SCD activity: Microsomes were prepared from hearts of PBS-treated, ob/ob, ob/ob pair-fed (PF), and leptin-treated (ob/ob-Leptin) mice, and SCD enzyme activity was determined by measuring the incorporation of radioactivity in oleoyl-CoA using [1-$^{14}$C]stearoyl-CoA as a substrate. The reaction products were separated by TLC, and the radioactivity was quantitated. Each value represents the mean±S.E. (n=4). B, Levels of monounsaturated fatty acids in the hearts of ob/ob mice: Total fatty acids were extracted from heart of ob/ob mice treated with either leptin or PBS and wild type controls quantitated by GLC as described in the example below. *, $p<0.05$ versus wt-PBS; #, $p<0.05$ versus ob/ob-PBS. C, Total RNA was prepared from hearts of PBS or leptin-treated ob/ob mice and used to measure SCD1, SCD2, and SCD4 mRNA levels by quantitative RT-PCR analysis. The fold change relative to that of wild type was calculated after correction for the levels of cyclophilin used as a standard. Each value represents the mean±S.E. (n=4).

Numerous dietary studies indicate that hepatic SCD activity increases when animals are fed with high carbohydrate fat-free diets, whereas it decreases when polyunsaturated fatty acids are ingested (Ntambi, J. M. and Bene, H. (2001) J. Mol. Neurosci. 16, 273-278; and Ntambi, J. M. (1992) J. Biol. Chem. 267, 10925-10930). These effects are thought to be mediated, respectively, through SREBP-1c induction by insulin and inhibition of SREBP-1c expression and protein maturation by polyunsaturated fatty acids (Repa, J. J. et al. (2000) Genes Dev. 14, 2819-2830). In addition, LXRα with or without the involvement of SREBP-1c can induce hepatic SCD1 gene expression by cholesterol (Repa, J. J. et al. (2000) Genes Dev. 14, 2819-2830; and Kim, H. J. et al. (2002) J. Lipid Res. 43, 1750-1757). To determine whether mSCD4, like mSCD1, is regulated by a high carbohydrate fat-free diet and polyunsaturated fatty acids and by the LXRα agonist T0901317, 129SV mice were fed either a high carbohydrate fat-free diet or a chow diet containing 0.025% T0901317. As shown in FIG. 5A, the high carbohydrate fat-free diet induced the expression of mSCD1 and mSCD2. Supplementation of the high carbohydrate fat-free diet with fish oil, a rich source of polyunsaturated fatty acids, repressed expression of mSCD1 and mSCD2, to a smaller extent, but had no effect on mSCD4 levels (FIG. 5B). Mouse SCD1, SCD2, and SCD4 were induced by the LXRα agonist 18-, 12-, and 60-fold, respectively (FIG. 5C). These experiments illustrate the tissue-specific modulation of the SCD isoforms by particular dietary factors.

ob/ob mice have a mutation in the leptin gene and are a model of obesity, insulin resistance, and diabetes. Previous studies showed that hepatic mSCD1 and mSCD2 expression were induced in the liver of ob/ob mice but were decreased when ob/ob mice were treated with leptin (Cohen, P. et al. (2002) Science 297, 240-243). We analyzed the mRNA level of the SCD4 isoform in the hearts of leptin-deficient ob/ob mice and ob/ob mice treated with either PBS or leptin. As an additional control, RNA isolated from saline-treated ob/ob mice that were pair-fed to the leptin treated group for 12 days was also analyzed. Pair-fed mice are given the same amount of food that leptin-treated mice voluntarily consume, allowing one to dissociate the effects of reduced food intake from those of leptin per se. After 12 days of treatment, food intake in the untreated wild type and ob/ob controls was 4.4±0.2 and 6.4±0.2 g, respectively (p<0.04), whereas the leptin-treated and pair-fed mice ate 1.2±0.1 and 1.1±0.1 g, respectively (p<0.001 for both leptin and pair-fed). By the end of the treatment period, leptin-treated ob/ob mice had lost a 34±0.8% of their initial weight as compared with 23±1.2% for pair-fed mice (p<0.002), confirming that leptin has specific metabolic actions distinct from its anorectic effects. SCD activity was elevated 3-fold in ob/ob hearts relative to the wild type controls and was completely normalized to wild type levels in leptin-treated ob/ob mice (FIG. 6A). SCD activity was reduced but to a lesser extent in the pair-fed ob/ob mice (FIG. 6A). To assess the effects of elevated SCD activity in the heart and its specific down-regulation by leptin, a separate and identical time course was performed. As expected from the SCD activity, ob/ob hearts were found to have a high 18:1 content that was reduced to levels comparable with those in wild type mice upon leptin treatment (FIG. 6B). To determine which SCD isoform(s) accounted for these effects, we measured RNA levels of mSCD1, mSCD2, and mSCD4. Unlike mSCD1 and mSCD2, which were not induced in the hearts of ob/ob mice, mSCD4 mRNA levels were increased 5-fold (FIG. 6C). The SCD4 mRNA levels were decreased by greater than 75% in leptin-treated ob/ob mice, whereas the expression of mSCD1 and mSCD2 isoforms were unchanged (FIG. 6C). These observations suggest that mSCD4 is a target of leptin regulation in the heart.

Figure 7:
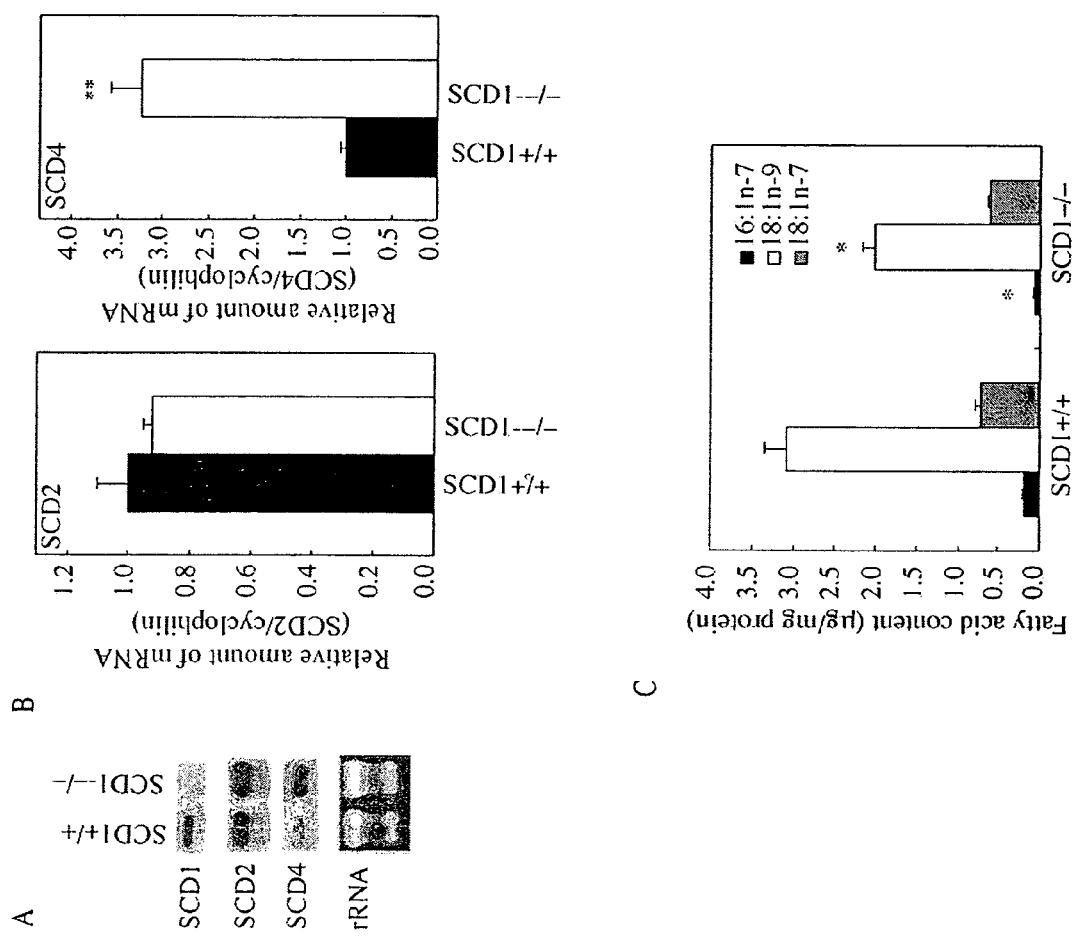
FIG. 7 shows mSCD4 and monounsaturated fatty acids levels in the hearts of SCD1−/− and SCD1+/+ mice. A, SCD4 mRNA levels in SCD1−/− mice: Total RNA prepared from hearts of SCD1−/− or SCD1+/+ mice was used to measure the SCD2 and SCD4 mRNA levels. The fold change relative to that of wild type was calculated after correction for loading differences with rRNA. B, Quantitative RT-PCR analysis: The fold change relative to that of wild type was calculated after correction for the levels of cyclophilin used as a standard. C, levels of monounsaturated fatty acids in the hearts of SCD1−/− and SCD1+/+ mice: Total fatty acids were extracted from heart of SCD1−/− and SCD1+/+ mice and quantitated by GLC as described in the example below. *, $p<0.01$; **, $p<0.001$ versus SCD1+/+ (Student's test).

We previously showed that administering leptin to ob/ob mice reduced mSCD1 expression in liver (Cohen, P. et al. (2002) Science 297, 240-243). To determine whether mSCD4 could compensate for mSCD1 deficiency in the heart, we analyzed the mRNA levels of mSCD4 in SCD1−/− mice. Northern blot analysis (FIG. 7A) and quantitative RT-PCR (FIG. 7B) using an mSCD4-specific DNA probe and primers showed that mSCD4 mRNA levels were induced 3-fold in hearts of SCD1−/− relative to the SCD1+/+ mice (FIG. 7A). SCD2 expression was not altered between SCD1−/− and SCD1+/+ mice. The amounts of C18:1 and C16:1 monounsaturated fatty acids were reduced by only 30% (FIG. 7B) in hearts of SCD1−/− mice compared with a greater than 70% reduction in livers of SCD1−/− mice (Cohen, P. et al. (2002) Science 297, 240-243), where SCD1 is the major isoform expressed.

These observations suggest that mSCD4 synthesizes the bulk of monounsaturated fatty acids in the heart and that elevated expression of SCD4 is expected to be responsible for the development of the "fatty heart" observed in ob/ob mice. Previous studies have shown that accumulation of lipid in the heart can have deleterious consequences, analogous to those of fatty liver (Minokoshi, Y. et al. (2002) *Nature* 415, 339-343; Atkinson, L. L. et al. (2002) *J. Biol. Chem.* 277, 29424-29430; Zhou, Y. T. et al. (2000) *Proc. Natl. Acad. Sci. U.S.A.* 97, 1784-1789; and Unger, R. H. (2002) *Annu. Rev. Med* 53, 319-336). Our observations indicate that SCD4 is the SCD isoform that is the target of leptin signaling in the heart. Therefore down-regulation of SCD4 expression by leptin is expected to be one of the mechanisms by which leptin depletes lipid from the heart and exerts its anti-lipotoxic effects.

The present invention is not intended to be limited to the foregoing example, but encompasses all such modifications and variations as come within the scope of the appended claims.

We claim:

1. A method for identifying an agent that can modulate an enzymatic activity of a stearoyl-CoA desaturase 4 (SCD4) protein comprising SEQ ID NO:2, the method comprising the steps of:

provinding a preparation that contains an SCDA protien comprising SEQ ID NO:2;

contacting the preparation with a test agent;

measuring the SCD4 enzymatic activity and comparing the activity to that of a control preparation that is not exposed to the test agent wherein a higher or lower than control activity indicates that the agent can modulate the enzymatic activity of said SCD4 protein.

2. The method of claim 1, wherein the preparation that contains an SCDA protein comprising SEQ ID NO:2 is a microsomal preparation.

3. The method of claim 2, wherein the microsomal preparation is derived from mouse heart tissue.

4. The method of claim 2, wherein the microsomal preparation is derived from cells that are genetically engineered to express the SCD4 protein comprising SEQ ID NO:2.

* * * * *

UNITED STATES PATENT AND TRADEMARK OFFICE
CERTIFICATE OF CORRECTION

PATENT NO. : 7,285,395 B2
APPLICATION NO. : 11/147606
DATED : October 23, 2007
INVENTOR(S) : James M. Ntambi and Makoto Miyazaki It is certified that error appears in the above-identified patent and that said Letters Patent is hereby corrected as shown below:

Col. 5, Line 15 "a CDNA" should be --a cDNA--

Col. 11, Lines 21, 23 "MRNA" should be --mRNA--

Col. 13, Line 7 "$^{32}$p" should be --$^{32}$P--

Col. 15, Line 29 "MRNA" should be --mRNA--

Col. 20, Lines 1, 4 "MRNA" should be --mRNA--

Col. 23, Lines 37, 41 "MRNA" should be --mRNA--

Col. 43, Line 26, Claim 1 "an SCDA protein" should be --an SCD4 protein--

Col. 44, Line 23, Claim 2 "an SCDA protein" should be --an SCD4 protein--

Signed and Sealed this

Thirtieth Day of September, 2008

JON W. DUDAS
*Director of the United States Patent and Trademark Office*

SEQUENCE LISTING

```
<160> NUMBER OF SEQ ID NOS: 13

<210> SEQ ID NO 1
<211> LENGTH: 3099
<212> TYPE: DNA
<213> ORGANISM: Mus musculus
<220> FEATURE:
<221> NAME/KEY: CDS
<222> LOCATION: (167)..(1225)

<400> SEQUENCE: 1
acagcagaac tgactggtga cacctgcaca gttagccggg catcaacgca gtacacacag      60
cgcacagtgg gctctggact caacgcttca ccgatcctca gtcgctgcag acctggacct     120
tgctctctct gccttcacaa gaggatctag gcttccaagg agcaag atg acg gcc       175
                                                    Met Thr Ala
                                                     1 cac ttg cca caa gag atc tcc agc agg tgt agc act acc aac atc atg      223
His Leu Pro Gln Glu Ile Ser Ser Arg Cys Ser Thr Thr Asn Ile Met
    5                  10                  15 gaa ccc cac tcc cgg aga cag cag gat gga gaa gag aag atg ccc ctc      271
Glu Pro His Ser Arg Arg Gln Gln Asp Gly Glu Glu Lys Met Pro Leu
20                  25                  30                  35 cag gca gaa gat atc cgg cct gaa ata aaa gat gat ctg tat gac ccc      319
Gln Ala Glu Asp Ile Arg Pro Glu Ile Lys Asp Asp Leu Tyr Asp Pro
                40                  45                  50 agc tac cag gat gag gag gga ccc ccg ccc aag ctg gag tac gtc tgg      367
Ser Tyr Gln Asp Glu Glu Gly Pro Pro Pro Lys Leu Glu Tyr Val Trp
            55                  60                  65 agg aac atc atc ttc atg gcc ctg ctg cac gtg gga gcc ctg tac ggg      415
Arg Asn Ile Ile Phe Met Ala Leu Leu His Val Gly Ala Leu Tyr Gly
        70                  75                  80 atc aca ctg gtt ccc tcc tgc aag gtc tac acc tgg ctc ttg gga gta      463
Ile Thr Leu Val Pro Ser Cys Lys Val Tyr Thr Trp Leu Leu Gly Val
    85                  90                  95 ttc tac aac gtg gtt gcc ggt ttg ggc atc aca gcc gga gcg cat cgc      511
Phe Tyr Asn Val Val Ala Gly Leu Gly Ile Thr Ala Gly Ala His Arg
100                 105                 110                 115 ttg tgg agc cac cga acc tat aaa gca agg ctg ccc cta cgc atc ttc      559
Leu Trp Ser His Arg Thr Tyr Lys Ala Arg Leu Pro Leu Arg Ile Phe
                120                 125                 130 ctc atc atg gcc aat acc atg gct ttc cag aat gac gtg tat gaa tgg      607
Leu Ile Met Ala Asn Thr Met Ala Phe Gln Asn Asp Val Tyr Glu Trp
            135                 140                 145 gcc cga gat cac cgc gcc cac cac aag ttc tca gaa aca cac gcc gac      655
Ala Arg Asp His Arg Ala His His Lys Phe Ser Glu Thr His Ala Asp
        150                 155                 160 cct cac aat tcc cgc cgt ggc ttc ttc ttc tct cac gtg ggt tgg ctg      703
Pro His Asn Ser Arg Arg Gly Phe Phe Phe Ser His Val Gly Trp Leu
    165                 170                 175 ctt gtg cgc aaa cat ccg gct gtc aaa gag aag ggc aaa aac ctg gac      751
```

```
                                                            -continued

Leu Val Arg Lys His Pro Ala Val Lys Glu Lys Gly Lys Asn Leu Asp
180                 185                 190                 195 atg tct gac ctg aaa gcc gag aag ctg gtg atg ttc cag agg agg tac      799
Met Ser Asp Leu Lys Ala Glu Lys Leu Val Met Phe Gln Arg Arg Tyr
                    200                 205                 210 tac aag cta gct gtc acg ctc atg ttc atc att ctg ccc aca ctg gta      847
Tyr Lys Leu Ala Val Thr Leu Met Phe Ile Ile Leu Pro Thr Leu Val
                215                 220                 225 ccc tgg tac ttg tgg ggt gag act ttt caa cac agc tta tgc gtc tcg      895
Pro Trp Tyr Leu Trp Gly Glu Thr Phe Gln His Ser Leu Cys Val Ser
            230                 235                 240 aat ttc ctg cgg tat gct gtg ctt cta aac ttc act tgg ctg gtg aac      943
Asn Phe Leu Arg Tyr Ala Val Leu Leu Asn Phe Thr Trp Leu Val Asn
245                 250                 255 agt gcg gcc cac ctc tac gga tac cgg ccc tat gac agg ggc att ggt      991
Ser Ala Ala His Leu Tyr Gly Tyr Arg Pro Tyr Asp Arg Gly Ile Gly
260                 265                 270                 275 gcc cgg gag aat ccc ttc gtt tca atg gca tct tta ggc gag ggc ttc     1039
Ala Arg Glu Asn Pro Phe Val Ser Met Ala Ser Leu Gly Glu Gly Phe
                    280                 285                 290 cac aac tac cat cac acg ttc ccc tac gat tac tct gtc agt gag tac     1087
His Asn Tyr His His Thr Phe Pro Tyr Asp Tyr Ser Val Ser Glu Tyr
                295                 300                 305 cgc tgg cac atc aac ttc acc acg ttt ttc atc gac tgc atg gct gcc     1135
Arg Trp His Ile Asn Phe Thr Thr Phe Phe Ile Asp Cys Met Ala Ala
            310                 315                 320 ctg ggc ctg gct tac gac cgg aag aaa gta tct aag gcc gtt gtc tta     1183
Leu Gly Leu Ala Tyr Asp Arg Lys Lys Val Ser Lys Ala Val Val Leu
325                 330                 335 gcc agg att aag aga act gga gat ggg agt cac aag agt agc               1225
Ala Arg Ile Lys Arg Thr Gly Asp Gly Ser His Lys Ser Ser
340                 345                 350 tgagtgtggg gtcatctggg tctctgttcc ataaaacaac tgggccaaca tttaatttc     1285 tgttaactac tgaataatgc taccaaagcc ctctcctgaa cttttttttt taggggagg     1345 ggagggtaca tggtctctct gtctctctgt cttgtctgta tctctgtgtc tctgtgtctg   1405
tctctgtctc tctctctcta gtctatacta tagaccaggc tggcttcgaa ctcacagaga   1465
tcttcctgcc tccgcctccc aattgttggg attaaagggg tgtatcactg tgcccagctc   1525
tgcgaagtct tgtcaaatgt tcaaggcaac tctccttat gaccccttg tcctctagtc    1585 ccatccccac ccttcgttcc tactatgctt gtctttcttt tctccttctc taagaagcag   1645
ccagtgagtg cttggccaac ctccccaagg cttcacagcc tttctgttgt ctcaaagtaa   1705
ggaccttcat catggacagt tctctgccta ggtatctgtc taaagctatc agtacaacaa   1765 aacctttag ggaatgtctt cttaattgcc gttagttcat gcttttctga agaaaagggg    1825
gaaaatagca tcagttgtca tagaagtgct aaaggtggag aatcctcagg tgggaaagca   1885
tgcagagtat gactcagaag cagggggacc atcaaggtag gaagtgactc agtagggagt   1945
actcaccaaa ataagacctc ccacagacag agcccagaca cagagcagga aacggccgtt   2005
gaaagtggcc atgctagaac acaatagaat gtctctgcag ctcagtctgg tccaagccag   2065
aagtaaagga aaaacaattc agttagtagg aaaagagatt tctcctgaga cagggttttt   2125
gtttgtttgt ttgtttgttt gttgttgttt tctgtattga caaggaacat tgttatgcca   2185
cagaacaaga aggcttcggc ttggttaaaa aaaacagaa aactcataga ttccacaagc   2245
tacacatcca atctgtttta cacttctctt ctgcctgcct tgcgttgtca atgttattta   2305
```

-continued

```
tgttctgctc tcatagtgat tgggtaacta tagcaacccc aaacatccca actggaagga    2365
ttgtaggcaa agttgggtca aacctaaaat catgtagacg attgtttaga gcagggaggg    2425
aggtgtttca ctgagtcctc tgagaaggtt ccagaagctt tagaacagag ggttacttgg    2485
gtttcctgta gctcccaccc ctgagaagag agggaagtct gatggccagt atcagtagtc    2545
acttcagaag aaatagcttt gcaaagagag agagctctga aacacattg tgctgtgggg     2605 gctccagaag ttactgagtt actaagtatt gagagagtag caaactcagt gctccaaggt    2665
atgctagtca taaaacagag agcgacattc ctccacccac cgcttcctgg gttcaaggag    2725
tgttcattca agaaagtcac cctgacccac cctgaccatt gctggaaccc gctatgcaaa    2785
ggtgctattg ttaggggctc ttagaaactg tcttgagaaa taaccctcac aattaccagg    2845
tattccttgt gacacctgtg actttgtact tccttgtgac tcttgactgg tattttttggt   2905 attttccaac aacgcccttc ccacctcctt gagttgtggt ttcttccttt aaatacccc     2965 ttatccagct acttggggtg ccccttatc cagctacttg gggtacttgg ggtacttgta     3025
tgatcgtgga cccgagagcg ctcttgaata aaaaaatcct cttgcaaaaa aaaaaaaaa     3085 aaaaaaaaaa aaaa                                                      3099
```

<210> SEQ ID NO 2
<211> LENGTH: 353
<212> TYPE: PRT
<213> ORGANISM: Mus musculus

<400> SEQUENCE: 2

```
Met Thr Ala His Leu Pro Gln Glu Ile Ser Arg Cys Ser Thr Thr
1               5                   10                  15

Asn Ile Met Glu Pro His Ser Arg Arg Gln Gln Asp Gly Glu Glu Lys
            20                  25                  30

Met Pro Leu Gln Ala Glu Asp Ile Arg Pro Glu Ile Lys Asp Asp Leu
        35                  40                  45

Tyr Asp Pro Ser Tyr Gln Asp Glu Gly Pro Pro Lys Leu Glu
    50                  55                  60

Tyr Val Trp Arg Asn Ile Ile Phe Met Ala Leu Leu His Val Gly Ala
65                  70                  75                  80

Leu Tyr Gly Ile Thr Leu Val Pro Ser Cys Lys Val Tyr Thr Trp Leu
                85                  90                  95

Leu Gly Val Phe Tyr Asn Val Val Ala Gly Leu Gly Ile Thr Ala Gly
            100                 105                 110

Ala His Arg Leu Trp Ser His Arg Thr Tyr Lys Ala Arg Leu Pro Leu
        115                 120                 125

Arg Ile Phe Leu Ile Met Ala Asn Thr Met Ala Phe Gln Asn Asp Val
    130                 135                 140

Tyr Glu Trp Ala Arg Asp His Arg Ala His His Lys Phe Ser Glu Thr
145                 150                 155                 160

His Ala Asp Pro His Asn Ser Arg Arg Gly Phe Phe Phe Ser His Val
                165                 170                 175

Gly Trp Leu Leu Val Arg Lys His Pro Ala Val Lys Glu Lys Gly Lys
            180                 185                 190

Asn Leu Asp Met Ser Asp Leu Lys Ala Glu Lys Leu Val Met Phe Gln
        195                 200                 205

Arg Arg Tyr Tyr Lys Leu Ala Val Thr Leu Met Phe Ile Ile Leu Pro
    210                 215                 220

Thr Leu Val Pro Trp Tyr Leu Trp Gly Glu Thr Phe Gln His Ser Leu
```

```
                225                 230                 235                 240
Cys Val Ser Asn Phe Leu Arg Tyr Ala Val Leu Leu Asn Phe Thr Trp
                    245                 250                 255
Leu Val Asn Ser Ala Ala His Leu Tyr Gly Tyr Arg Pro Tyr Asp Arg
                260                 265                 270
Gly Ile Gly Ala Arg Glu Asn Pro Phe Val Ser Met Ala Ser Leu Gly
            275                 280                 285
Glu Gly Phe His Asn Tyr His His Thr Phe Pro Tyr Asp Tyr Ser Val
        290                 295                 300
Ser Glu Tyr Arg Trp His Ile Asn Phe Thr Thr Phe Phe Ile Asp Cys
305                 310                 315                 320
Met Ala Ala Leu Gly Leu Ala Tyr Asp Arg Lys Lys Val Ser Lys Ala
                325                 330                 335
Val Val Leu Ala Arg Ile Lys Arg Thr Gly Asp Gly Ser His Lys Ser
                340                 345                 350
Ser
```

<210> SEQ ID NO 3
<211> LENGTH: 10166
<212> TYPE: DNA
<213> ORGANISM: Mus musculus

<400> SEQUENCE: 3

```
agtgtttttt tatcttatat tatagctaga aaatggaaaa ttctttgatt ggtctaaatc     60
tataagactc atgtagccac ttcattgggt tttttactgg tcttagaggt gtaatatact    120
ctgcgtgtct tcatcacaag agtattagct tataagttat tgggtatgat caaaaaggtg    180
taacactggt tactagaaag ttagctttaa gttggtaact caggtttgga gtctttcaaa    240
catgttgcat aaagcaggcc aaaaaactag gcctctaagg atacttctag ttgagataat    300
atttaatgtg gattccttatc ctaaaaggta gacttaaaga taagatttaa agcaatgtct    360
ctttaatgaa gcattaaaac ttgcactgtc atgcattcat aggtataaat tggcagccaa    420
attttgtaat gtgatagtga tgtttctaac attgattcta aggttataaa ttgttttgaa    480
attgggtttt gctttcccaa ggttgtagat attattctaa tgttgcaaaa gaaacttaaa    540
aatcatggtt aaaattgcca gtgttctatt gactgcagct tgcagtttga tcacaagctt    600
aagattttaa actcacccat atattgttaa ttaagattat tacaagagta atcattgaga    660
cgggtgtggt ggcacacgcc ttttatccca gcacttggga ggcagaggca ggaggatttc    720
tgagttcgag gtaagcctgg tctacaaagt gagttccagg acagccaggg ctatatagag    780
aaaccctgtc tcgaaaaaca aaaaaacaaa acaaaacaaa aaaaaaaaag agtaatcatc    840
ttatgagagc gctacaaaac taagacagag ttatctagat atgtttgttt ttgtacataa    900
attagaccct cagacagtag attttgctta tggttgctgc ctggcaggag actacagtac    960
aggcaatttt tttttttttt ttttttttta cagcaccaaa gttataaagt aagttttaag   1020
tataagtcat tttaagaaag actatccaaa attagaggca tggacagttg aattgttttcc   1080
ccagaatttg tcctcattgc aggagggcca agatgctcag attaaaaaaa atttatgtt    1140
ttgagttaat gcaaagttcg agcagcctct gcggggtggg gtggagggggt ggggggtgg    1200
gtgtgtgtgt gactttcttt tgttttgcaa acagtgcctg gggaagttct tgccagcctt    1260
caggggaatt tctaaaagaa cactgttgca gatctatcca gatgttgttc taaataaagt   1320
tctaattcaa agtttataaa gggtcaatca ggctgtagaa tttatcaaga cattacagtt   1380
```

```
tgacttgcct acttcatgta aagttattat aggcttaaaa gtttgttttt tcctttgaat    1440
tctgataatt ataaagagtt ttgcttctag tgaactggta atcactggaa aattttgcct    1500
ctaggtatgg ctaatatagc tttacattat gtaagaaaaa attttttattg cctctgcttc    1560 tatataagaa gctaagagct tgaattttc agtgtatatt gtttcctaag tggaaagtat    1620
tttaaagcta atggctctca agggaagttt actttaaatc tttgctctca tacaatgagc    1680
tttaaagttc tggggagtag ctgttgctcc agaaaagatt cagaggcaat atcttttaa    1740 tatttagggt tttagttata ctataaaatt ttggtacaga aaatctaaga acgaaaaatt    1800
gatttgcttc aaaattttat tttcaaaagc ttccaggaga tgttaattgg ctaagacctc    1860
accttaaact caccacagga gaacttaagc ctttgttagg tgctattaag tgagacacaa    1920
atgaactggc aaagaacaaa aggctttgca gaaaataaag aaagctttta taattgttat    1980
caattataat caatagtaat taaatattag ctgcttattt tagttatggt tattaaatgt    2040
gcccacagca attctttggc aagagaaaaa tttaatgtaa aatcatcttt ctttgcctca    2100
aagtaaagtt ttaacatcct tttaaggctg ctgtggtgct aataaagaat tgtaagataa    2160
ctttgtgtat tttagaaaac ctataacaaa aaattgtgtc ttaagaacct gacaaagtgt    2220
ctgttccttg ttccaatagc aattaatttg gttattgcag aatattgata tttggcctat    2280
tgcacaccat catttaaaat aaaattgata atcattatcc taaagataag ttaaaaattg    2340
tttttatgca tgcttttgta ccttctataa atccatgcat gtatgcatcc catttactgt    2400
gtttaaaaac agcccttcta tgggagaaaa gtatatgtga attggatcac acgcttattc    2460
ttttgagttt cttcctgctt cagcatagat aattaaattg tgtgctgtag atggtgtttt    2520
aaaatgttga ataatcaagc tttaatttgt atgttaatta tcaatgtata tctcagagct    2580
tacaattgct taaaattgtt cttctctcag atactataaa ttctcaaatt tgcaatggtt    2640
tatgcataca taactcataa gaaaaaatgc tgctctttta agaagactgt ttttggacat    2700
ttaataaaat tttctggatt gtctggacaa gacccttaa ggcaatgcca tgctagattt    2760
atatctcagg cagatacagg ccttacataa gaataatctc attctttatt taatcaaaac    2820
agtaatggtt taagataata ttttggtatt tttagagaag gtgcatatca aattgtgaaa    2880
gagttgttct tggtgtcctc aattcctacc tgtttccaca taatggcggg accattagct    2940
aatacgtgga atggttcccg tcttaatatt ggggaagaga gggagtgctt ctgttttttc    3000
cacagaatgc tgcaggagta tgctagcttc caatgtgaca ggctgacctg tgggttcctg    3060
agcaccctga cagtggttac aggaaagctg tattgagcgc acagaggagg aggaaattgg    3120
agagcagcca tttgcaaaca agatgaagaa acttcctatc cccgccatgg gctacagcaa    3180
ggagagctga cctggtgtca acttggggac aactaaaaat gatgactcgt gaggcagagg    3240
gactgctaca gagtattgga caagatttcg tcagagacac tgttttggc cattcaggcc    3300 aactccccta tagctgtaaa aacttgtgta ccttacctgt atgctataat gttagataat    3360
tttaagagtt aagatcacca atcttggcaa gtcttttcat attcattgta attcttgtca    3420
aataactaat tgtgtagatc ctaatttaga taagaaatct gctgttatga ttttgttaaa    3480
gagatctgct tatgttttgc tgccaattag agttaggaaa tgatccttgg tttaaaaatc    3540
tgggaatgca aactttgaaa aggtatctac cacagctttta gatcagcagc tgcatactgc    3600
tcattttgtt aatgataagc ataggaatat ttccatagcc ttgtcaaagc tgcatattat    3660
agataaaaat tggaggcaaa ggttaatgtc ttagaagtag tagtcttagc aatagggcag    3720
gacatagcat atattaaggc tagaaaggca gaaatttcag atattagcaa aagtcacttg    3780
```

-continued

```
gacacttgga acattgatga attggccaga gattaaaaca acagcaacaa caacaacaac    3840
aacaacaaca acaacaacaa caaactaagt gcattgaatc ccctggattg ggttcaatat    3900
ataatcctac ttgctactat tattggcatt attttcttag taatcattgt gtttccactc    3960
atctttagag cactcttgag atctgtagct acgatgaggt gggacattcc ggaacttcgg    4020
cagaaatata aaaagatag gggaagaatg ctacacacac tccagtgaag tttgcttggc     4080
aggcttagag gcctgggagc actcacgagg caaagagttt cacggaaact cacctcctgg    4140
aactttggcg tcctcataac ctgtacccta tccccataac tcatacccta tcctcgagtt    4200
agtctggtgt atggatccac gtgctctctt ttagtattat tttattataa gtgccttta    4260 agattgaatt ctgacatagc taagcctttg ccagtgttac aatgttccag aaacccttg     4320 aagccaacaa actgggaatt cagtaggaat tcagtgagaa ggttaggtaa cattcaagtt    4380
tacttctagt agagacagtg aaactaatga ggcattacac agaacgagat agaatagctc    4440
agggctagtc tgcagagtga tcacttggga cagtagccag tcttacccag acaagggaat    4500
tcaccagggc ctagcgatta ggtgggttta ccatgagaaa gctagggaat ctcactgaga    4560
caggtttctt cattaggccc aaagaaatca ggcaggacta tggagcataa aattttttt    4620 atgctgaaaa agtaaaacgt aaaaacaaaa ttctaggcct ttgggagtgt ggcctttgtg    4680
gctcagtgct ccgaggtgtg ctggtcataa acagatagc aacattcctc caccacctgc     4740
ttcctgggtt caaagagtgt taattcaaag aatgtgctat tgttagggc tcttagaaac      4800 tgtcttgaga ataaccctc acaattacca ggtattcctc gtgactcttg tgactttgca     4860
cttccttgtg actcttaact ggtattttttg gtattttcca acaatgccct ccccacttcc   4920
ttgagttgtg gtttctccct ttaaatacc ccttatccag ctactcgggg caccacggtc     4980
ctctacccct gcgtggtgta tgatcgtgga cctgagagcg ctcttgaata aaaatcctct    5040
tgcagtttgc agcaagaccg tttcttgtgg gtgattttgg ggtgttgcct ctcctgagtc    5100
agaacatggg ggagtcctca cgttgtgagt cttcaatgc cttggtccag ctattttat      5160 tatataatca gggaggaagc aggctgatcc agactttgac cttgcagcca ctaagaagga    5220
gattacctag ggggtagcct tccgacctag atggctctat ggttctgtca cctgtcactg    5280
ctctcctcaa agacactgct acctgctgag aggcccctga ggcattctga ggaacatcct    5340
atcctgcaca ggctggctcc agacaccaag aatgaactgg cggggatgg gacttccccc     5400 ttataagcac actctcttag taaactcgtg ggccttacac agaattgtgt cttggtctcc    5460
attatctctc tcaccgtcta agtctttttc agccccaaac tgcctcccag gtgtacctgg    5520
ttcaagtagg ctgtgggccg gcatacaaca aagaacattt gtttctcttg aaaagcctg     5580 gagtttggtt tccagcaccc atgtaacagt tcataaccat ctgtaactcc agttccaaag    5640
gatcctgtgc attctttcgg cttccatgca cactgtacac acatgtagtg catagacata    5700
catgtgagga aacactcata ctcataaact aaaaataaac acaactttaa cataattaaa    5760
atttaaatgt ccattttgc tttgttgtat cacagagaag agaattgtgt agatcaaagc     5820
caaaggcagg atgtgagtag gaaaagaaaa atcggataat ttgtgcttca gtaaaacttg    5880
aaatagttgt gcttccaaaa gagactaaaa gaaagtgaaa ggagccaagc agtgatggtg    5940 cacacctta attccagcac tggggaagca gaggcaggtg gatctctgtg agttcaaggc     6000
cagcctgatc tgctgatctt ctaattttgt cttccagttt ccttggttat gtcatagact    6060
tcctttcaat cagagccaat agcatagcta atgaaggaaa gggggagtta ttgtagattt    6120
```

```
cataagtgaa gggtaatatt atgtataaaa ggccatagct gaaagtgcct ttgtccttta    6180
tccccaggga gggggacaaa gtgaagtgaa aaggtgtctg tgtgtgtatc tgtgtgtgtc    6240
cttgactgcc cttcaccttg gttttgaaac agtcttttat tgagcctggt gctcacagat    6300
tggcttgctt ggctggcagg ccacacaccc cagcatcctt ctccctcttt cccaggcttt    6360
catggtctgg gagtagaggc ctgccctatc ccttcttgtt ttgtatgtgg gtgctggagg    6420
tctggactca ggtcctcatg tttatccact gagctatgtg cccagcccct agttgatttt    6480
ttttaaactt tgatgaataa ttaacttagc ctacgtgtct ccattgccgg ctgcttctac    6540
cctccatggt tgtctgactt ccatgtgtta ggtgaaaaac tgaaaatgca tgtataaaat    6600
gagccaagga aacttcagtt cagaccagat gtcctttacc tgccttttgt gtacctgagt    6660
ggctcacaga ttctcacaaa gatcccaaat tctaaagata ggcatcccca ccctataagg    6720
ctgtaggctg tataactggg tcatactcaa accccggtct gaggtcctgc tcttttttaca   6780
gaccctggat cattttagtt cagtgttctt gaaaaggaag gatgttgatt gtaaagatct    6840
ttcaaaacgt acacatgcag gctctaggtt caagtgttct gttccctcac tgagagcatc    6900
cctcagtgtg tgagaatttt tagcttagac ctttgtgtaa atatgatgaa aacggatttt    6960
gtttgttgtt gttttgagat agattctcaa ctctgtagct ctgactggct ggggactcat    7020
tgagtagacc aggctggcct caaagtcata gaaacccaac tgcctctgcc tcccaagtgc    7080
tgaaaaggat tttaattttt gttttgaaa cagagtctgg cttcatcacc caggatgtcc     7140
tcaagttggt catcctcctt cagcctccca aatgctggga ttaggcctga cgacatgtga    7200
gactgaattg tctgacctat ttgcccatca tctatctcca actgtgtgtt ggagtgtcgg    7260
aaggctcttt cctaaaaaca aaacccatga aatccccagc tactctagct gaggcagagg    7320
ggttcgatgt tccaagccag cctgagctac atagtgaaac ctttcaagaa acaacccagg    7380
gctgagaaat gtagctcagt ggtacagcac ttgcctggta tgtaccaggt tatgaatttg    7440
atcccccata gagccaaaag tacacaaaaa caagacacaa aaatctgccc tgacgaaagt    7500
cactgaagaa aacagtttct tgggagcgga aatctctgga tgatagatgc acacatttga    7560
tcttattggg tgccgataga ttgttcttta gaacagttgg gcaacttcca ggctcataag    7620
tgcccttcga gtctccattt ctctgcttcc tagccagccg tagataatgc catgcctact    7680
tttacaactg cagtagggg ttcctctagc tcgcatttac gaatttcatt tcaagcaaat     7740
cacagtcccc actggtccct tctcagatcc cgtaacttat ctctcttctg ggaagtgatc    7800
actgaataat taatgtctgt aagaaattct ataatgcact agagaaacca aggaaaggtc    7860
aggcagggct cctgccatga ggaggcttat ggtttacccg tgagatggac ttgcaaactg    7920
gttttttggtt ttttggtttt tttggttttt tggtttttttg gttttttggt ttttttgttt   7980
tttttggtt ttttggtttt ttggtttttt ggttttttgt ttttttggt ttttttggt      8040
ttttggtttt tttggttttt tggttttttg gttttttggt ttttggtttt ttggttttt    8100
tggttttttg gttttttggt ttttggtttt ttggttttt tggttttttg gttttttggt    8160
ttttggtttt tttggttttt ttggttttt ggttttttgg ttttttggt ttttggtttg     8220
tttttccaga caaggtttct gtctatagtc ctggctgtcc tggaacttgc ttggtagacc    8280
aggctggcct caaactcata gagatccacc tgcctctgcc tcccaagtgc tgggatgaaa    8340
aatgtacacc accatgccca gtgcaaacaa gtctcaatat ggctgttaaa ataaaattgt    8400
ggggtcaaag caaagcaaag tatgtgggga gccaaaagga ctgtggggtc cctcgctgtt    8460
tgataagagg ggaagaggat ggagaggcca aggaagcttt cacagaggga caagttggtc    8520
```

```
atgcttgccc tcatatagtc tcctttgtgt gtgtgtgggg gggaagtgta caggggagat    8580
gtctatctca ggagacccta gtgaatgcaa atccctgcag tttgagcttc ctcatcctgc    8640
tgtgaatcta ctgaagacgg cctgtgaagt cattttgtct tgggactcta ggccagcatc    8700
gctttccgag cagggtttga gcctgggctc tggcatcttg cctactatga tcagtttcta    8760
gctctgtgag tcactggctc ctgggaccac agacaaatta tctgagctct ctatatctca    8820
acttccttct ccttaaaaac cacaggtcat gggtcacggg gagactttt aaaaagttag     8880 tattagcttt tttttttttt ttttaaagtc attccatacc agctcagtct tcttatttca    8940
caggcaaacc tttgcacctc tgctgcctgt aaacgcctgt ctgaggttcc cacttttcc     9000 ttatagaaga ctcccaattc ccaacctgat gggagaatct tcagacctcc ctgcctgcag    9060
cagatgttcc gggggcagga acatagggaa gtaattaaat gctaatgtct ggaggtggtt    9120
atcccctgtg aaacgagtcc tatgactgag cgtgggctca gacactcagc cctgtgcgtg    9180
tgactgtgtg tgtgagctgg tcagagcatt ctgcgattct gctgaacatc ctgggcaggt    9240
gggtggggaa gagccgccac tggcttgaga tgctaagtaa gaaggcgggc tatgcacctg    9300
ctcttgtctc gagatctggg ggtggaggcc agtccacccc cccttacccc caccacacct    9360
gatgagtgga aagagaaggt ggaattgtgg tggacactga tgagctgtcc ccactgtgca    9420
actgccccag tgtgacacat ttgccaagca cctgtgttag tcctgggctt gaacttgact    9480 ctcaccccc agattcactc ttttcccact ttgtggacat tttctaccct ctatgaagct     9540
tgagaactgg accccagatt cctccagtca tgatgctggc agagacccag ggtccacaga    9600
gatgaaaccg aggaggttgg cacagagggc tgtctgccag cgagatagca gatttctgga    9660
tgccagagcc aggaagacaa gagagtaaca aattcctctg ctcagagctt gccagagtgc    9720
tgagaatact ccatctgtct aggaatgggg acaaaggtgg ctctctctta gtgtgtgcag    9780
catcccatag ccttgcctta ggtgaatgtg ggctttgctg gctgtcctcc cctctctcgc    9840
cttcagtctt tatctcctca tggggctgcc ttgactagcc agctctgaat tctttatccc    9900
ttgttggcag tcatgaagca catctgaaca aataccagac acagtcacca agtgccagct    9960
ctacataccc tttaaatcct gtgcctggaa acaacaacac acagcagaac tgactggtga   10020
cacctgcaca gttagccggg catcaacgca gtacacacag cgcacagtgg gctctggact   10080
caacgcttca ccgatcctca gtcgctgcag acctggacct tgctctctct gccttcacaa   10140
gaggatctag gcttccaagg agcaag                                        10166
```

<210> SEQ ID NO 4
<211> LENGTH: 28
<212> TYPE: DNA
<213> ORGANISM: Artificial
<220> FEATURE:
<223> OTHER INFORMATION: Synthetic oligonucleotide

<400> SEQUENCE: 4
tcctgctgtc tccgggagtg gggttcca                                        28

<210> SEQ ID NO 5
<211> LENGTH: 28
<212> TYPE: DNA
<213> ORGANISM: Artificial
<220> FEATURE:
<223> OTHER INFORMATION: Synthetic oligonucleotide

<400> SEQUENCE: 5
ttggccaacc tccccaaggc ttcacagc 28

<210> SEQ ID NO 6
<211> LENGTH: 35
<212> TYPE: DNA
<213> ORGANISM: Artificial
<220> FEATURE:
<223> OTHER INFORMATION: Synthetic oligonucleotide

<400> SEQUENCE: 6
acagcagaac tgactggtga cacctgcaca gttag 35

<210> SEQ ID NO 7
<211> LENGTH: 34
<212> TYPE: DNA
<213> ORGANISM: Artificial
<220> FEATURE:
<223> OTHER INFORMATION: Synthetic oligonucleotide

<400> SEQUENCE: 7
ccgagagcgc tcttgaataa aaaaatcctc ttgc 34

<210> SEQ ID NO 8
<211> LENGTH: 22
<212> TYPE: DNA
<213> ORGANISM: Artificial
<220> FEATURE:
<223> OTHER INFORMATION: Synthetic oligonucleotide

<400> SEQUENCE: 8
aggatggaga agagaagatg cc 22

<210> SEQ ID NO 9
<211> LENGTH: 24
<212> TYPE: DNA
<213> ORGANISM: Artificial
<220> FEATURE:
<223> OTHER INFORMATION: Synthetic oligonucleotide

<400> SEQUENCE: 9
agttgtttta tggaacagag accc 24

<210> SEQ ID NO 10
<211> LENGTH: 21
<212> TYPE: DNA
<213> ORGANISM: Artificial
<220> FEATURE:
<223> OTHER INFORMATION: Synthetic oligonucleotide

<400> SEQUENCE: 10
gctctctctg ccttcacaag a 21

<210> SEQ ID NO 11
<211> LENGTH: 25
<212> TYPE: DNA
<213> ORGANISM: Artificial
<220> FEATURE:
<223> OTHER INFORMATION: Synthetic oligonucleotide

<400> SEQUENCE: 11
tgttcctcca gacgtactcc agctt 25

<210> SEQ ID NO 12
<211> LENGTH: 60
<212> TYPE: DNA
<213> ORGANISM: Artificial

```
<220> FEATURE:
<223> OTHER INFORMATION: Synthetic oligonucleotide

<400> SEQUENCE: 12
ttgaattcac catgtaccca tatgacgtcc cggactacgc catgacggcc cacttgccac        60

<210> SEQ ID NO 13
<211> LENGTH: 30
<212> TYPE: DNA
<213> ORGANISM: Artificial
<220> FEATURE:
<223> OTHER INFORMATION: Synthetic oligonucleotide

<400> SEQUENCE: 13
ttgctcgagt cagctactct tgtgactccc                                         30
```